(12) United States Patent
Cong et al.

(10) Patent No.: US 10,043,280 B2
(45) Date of Patent: Aug. 7, 2018

(54) METHOD AND SYSTEM FOR IMAGE SEGMENTATION

(71) Applicant: SHANGHAI UNITED IMAGING HEALTHCARE CO., LTD., Shanghai (CN)

(72) Inventors: Lin Cong, Shanghai (CN); Wei Guo, Shanghai (CN); Qiang Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 50 days.

(21) Appl. No.: 15/297,301

(22) Filed: Oct. 19, 2016

(65) Prior Publication Data

US 2017/0109893 A1 Apr. 20, 2017

(30) Foreign Application Priority Data

Oct. 19, 2015 (CN) .......................... 2015 1 0679427
Oct. 19, 2015 (CN) .......................... 2015 1 0679631

(51) Int. Cl.
*G06K 9/00* (2006.01)
*G06T 7/00* (2017.01)
(Continued)

(52) U.S. Cl.
CPC ............ *G06T 7/0081* (2013.01); *A61B 6/032* (2013.01); *A61B 6/50* (2013.01); *A61B 6/5211* (2013.01);
(Continued)

(58) Field of Classification Search
CPC .......................... G06T 7/0081; G06T 7/0012
(Continued)

(56) References Cited

U.S. PATENT DOCUMENTS

2007/0047794 A1* 3/2007 Lang ....................... A61B 6/505
382/132
2008/0181481 A1* 7/2008 Hong ........................ G06T 7/12
382/132
(Continued)

FOREIGN PATENT DOCUMENTS

| CN | 102208109 A | 10/2011 |
| CN | 103778626 A | 5/2014 |
| CN | 104091337 A | 10/2014 |

OTHER PUBLICATIONS

International Search Report in PCT/CN2016/076358 dated Jul. 8, 2016, 4 pages.
(Continued)

*Primary Examiner* — Raj Chakraborty
(74) *Attorney, Agent, or Firm* — Metis IP LLC

(57) ABSTRACT

The present disclosure relates to a method and a system for image segmentation, the technique includes: obtaining a lung image and a lung model based on a plurality of chest image samples in a training set; pre-processing a lung image; acquiring a binary image of boundaries of the lung image; performing the generalized Hough transform on the binary image to locate initial boundaries of the lung image and obtain a Hough location; aligning the lung model to Hough location to obtain an alignment result; applying dynamic programming algorithm to the alignment result to obtain a segmentation result; and transforming the segmentation result back to the original coordinate system.

19 Claims, 23 Drawing Sheets

(51) Int. Cl.
*A61B 6/00* (2006.01)
*A61B 6/03* (2006.01)

(52) U.S. Cl.
CPC .......... *A61B 6/5258* (2013.01); *G06T 7/0012* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20061* (2013.01); *G06T 2207/30008* (2013.01); *G06T 2207/30048* (2013.01); *G06T 2207/30061* (2013.01)

(58) Field of Classification Search
USPC ......................................................... 382/131
See application file for complete search history.

(56) References Cited

U.S. PATENT DOCUMENTS

| | | | |
|---|---|---|---|
| 2011/0052018 A1* | 3/2011 | Blaffert | G06T 5/003 382/128 |
| 2013/0259352 A1* | 10/2013 | Wang | A61B 6/50 382/132 |
| 2014/0078320 A1* | 3/2014 | Hong | H04N 5/217 348/208.1 |
| 2014/0153797 A1 | 6/2014 | Wan et al. | |
| 2015/0363937 A1 | 12/2015 | Weistrand | |
| 2016/0117797 A1 | 4/2016 | Li et al. | |

OTHER PUBLICATIONS

Nritten Opinion in PCT/CN2016/076358 dated Jul. 8, 2016, 3 pages.
Cootes et al., Active shape models—their training and application, Computer vision and image understanding, 1995, 61 (1): 38-59.
Wang et al., Automated lung segmentation in digital chest tomosynthesis, Medical physics, 2012, 39(2): 732-741.
Shiraishi et al., Development of a digital image database for chest radiographs with and without a lung nodule: receiver operating characteristic analysis of radiologists' detection of pulmonary nodules, American Journal of Roentgenology, 2000, 174(1): 71-74.
Suzuki et al., Image-processing technique for suppressing ribs in chest radiographs by means of massive training artificial neural network (MTANN), IEEE Transactions on medical imaging, 2006, 25(4): 406-416.
Loog M and Ginneken B, Segmentation of the posterior ribs in chest radiographs using iterated contextual pixel classification, IEEE Transactions on Medical Imaging, 2006, 25(5): 602-611.
Li and Katsuragawa, Improved contralateral subtraction images by use of elastic matching technique, Medical Physics, 2000, 27(8): 1934-1942.
Lee et al., A nonparametric-based rib suppression method for chest radiographs, Computers & Mathematics with Applications, 2012, 64(5): 1390-1399.

* cited by examiner

METHOD AND SYSTEM FOR IMAGE SEGMENTATION

CROSS-REFERENCE TO RELATED APPLICATIONS

This application claims priority to Chinese Application No. 201510679631.5, filed on Oct. 19, 2015, and Chinese Application No. 201510679427.3, filed on Oct. 19, 2015, the entire contents of each of which are hereby incorporated by reference.

TECHNICAL FIELD

The present disclosure generally relates to a method and system for image processing, and more particularly, a method and system for segmenting lungs and/or ribs in medical images.

BACKGROUND

Lung segmentation is a step in post-processing of digital chest X-ray images (digital chest radiographs). The segmentation results may influence subsequence detection and analysis of lesions in lung. However, tissues of the chest may overlap with each other and affect the segmentation results. In addition, more X-ray may be absorbed in regions with higher density. Hence, ribs (a high density region) may absorb more X-ray and produce a bright region in a digital chest radiograph, while lungs (a low density region) may absorb less X-ray, and produce a dark region in a digital chest radiograph. Because of the uneven density distribution in the tissues in the chest, classic lung segmentation may create zigzag boundaries. Also, lower corners of a lung may not be segmented by classic lung segmentation.

Two types of approaches may normally be used for lung segmentation. The first type may be based on a rule level, such as a threshold segmentation approach, a region growing approach, an edge detection approach, a morphological filtering approach, etc. Due to the low quality of X-ray images, those approaches of this type may not be used for accurate lung segmentation. The second type may be based on pixel classification, such as a genetic algorithms approach, a neural networks approach, and a fuzzy clustering approach, etc.

In addition, ribs in posterior-anterior (PA) digital chest radiographs often overlap with lung abnormalities, such as nodules, and may cause these abnormalities to be unidentified, it is therefore beneficial to segment the ribs in chest radiographs and remove the ribs therefrom.

Segmentation of a rib in a digital chest radiograph may be performed using a learning-based approach, such as a neural networks approach, iterative contextual pixel classification (ICPC), etc. However, these approaches are mainly used for classifying bone area and non-bone area, and thus, it may need to train a classifier of this type with a plenty of different images in which ribs may be manually identified.

SUMMARY

The present disclosure provided herein relates to medical image processing. Specifically, the present disclosure relates to a method for segmenting lungs and ribs in medical images, e.g. digital chest radiographs.

In some embodiments, a method for segmenting lungs is provided. The method may include: obtaining a lung model; obtaining a chest image including a lung; pre-processing the chest image; acquiring a binary image including a boundary of the lung based on the pre-processed chest image; performing generalized Hough transform on the binary image to locate an initial boundary of the lung in the chest image to obtain a Hough location of the lung; aligning the lung model to the Hough location of the lung to obtain an alignment result; applying dynamic programming algorithm to the alignment result to obtain a segmentation result; and transforming the segmentation result back to a coordinate system of the chest image.

In some embodiments, the lung model may be obtained by: obtaining a training set, wherein the training set includes a plurality of chest image samples; selecting a first chest image sample from the training set; acquiring a first lung contour in the first chest image sample; selecting a plurality of the second chest image samples from the training set; acquiring a plurality of second lung contours, a second lung contour corresponding to a second chest image; processing the plurality of second lung contours to obtain transformed second lung contours; aligning the transformed second lung contours with the first lung contour; determining an average lung contour; determining a difference between the plurality of second lung contours and the first lung contour; comparing the difference with a threshold; determining that the difference is smaller than the threshold to obtain a first determination result; and designating, based on the first determination result, the average lung contour as the lung model.

In some embodiments, the obtaining the lung model may further include: determining that the difference is larger than or equal to the threshold to obtain a second determination result; performing, based on the second determination result, operations including designating the average lung contour as a previous average lung contour; performing rotation, scaling and translation transformation on the first lung contour and the plurality of second lung contours with respect to the previous average lung contour to obtain current transformed lung contours; aligning the current transformed lung contours with the previous average lung contour; determining a current average lung contour; and determining a difference between the rotation, scaling and translation transformation for the current average lung contour and the previous average lung contour; comparing the difference with the threshold; determining that the difference is smaller than the threshold to obtain a third determination result; and designating, based on the third determination result, the current average lung contour as the lung model.

In some embodiments, two lungs in two chest image samples of the plurality of chest image samples are each annotated by a same number of feature points.

In some embodiments, the feature points on the two lungs of the chest image sample are annotated at similar locations.

In some embodiments, the feature points are annotated at the corners, the highest point and the lowest point on a contour of each lung in the chest image samples.

In some embodiments, the pre-processing the chest image may include: filtering the chest image by a Gaussian filter to obtain a filtered image; subtracting the filtered image from the chest image to obtain a subtracted image; adding an average gray scale of the filtered image to the subtracted image to obtain a background removed image; and performing a bilateral filtering operation to the background removed image to obtain a pre-processed chest image.

In some embodiments, the pre-processing the chest image may further include: obtaining a template corresponding to the boundary of the lung in the binary image; identifying a gravity point of the template; identifying a first point other than the gravity point on the template; performing generalized Hough transform to locate a second point in the binary image that corresponds to the first point; determining, based on the second point, a third point in a Hough space; and increasing a gravity value of the third point by one.

In some embodiments, the acquiring a binary image may include applying a boundary edge enhancement operator to the chest image to obtain a gradient image; and generating the binary image based on the gradient image.

In some embodiments, the generating the binary image based on the gradient image may include designating pixels in the gradient image whose values are at least 15% of the highest values in the gradient image as belonging to the boundary of the lung.

In some embodiments, a method for segmenting ribs is provided. The method may include obtaining a chest image including a plurality of ribs; pre-processing the chest image; acquiring a binary image based on the pre-processed chest image; obtaining a plurality of rib templates; performing generalized Hough transform to obtain a gravity value based on each of the plurality of rib templates; selecting one of the plurality of rib templates as a representative rib template based on the gravity values; selecting a representative rib with respect to one rib in the binary image based on the representative rib template; generating a standard rib template based on the representative rib; performing generalized Hough transform based on the standard rib template to locate a lower boundary of a rib in the chest image to obtain a Hough location of the rib; aligning the standard rib template to the Hough location to obtain an alignment result; applying a bilateral dynamic programming algorithm to the alignment result to obtain a segmentation result; and transforming the segmentation result to a coordinate system of the chest image.

In some embodiments, the method may further include applying a Sobel edge enhancement filter to enhance the lower boundaries of the ribs.

In some embodiments, the value of pixels in a top section and a bottom section of the lung in the chest image is set to zero.

In some embodiments, the distance between two adjacent ribs is assumed to be ten percent of the height of the lung.

In some embodiments, the method may further include performing a bilateral dynamic programming algorithm to delineate the lower boundary and the upper boundary of a rib simultaneously, with a constrained dimension between the upper boundary and the lower boundary of the rib maintained to be a pre-set value.

In some embodiments, the constrained dimension has a value from eleven to twenty pixels.

In some embodiments, a system for segmenting lungs is provided. The system may include a storing module configured to store a training set and at least one chest image, wherein the training set has a plurality of chest image samples; an outputting module configured to display the plurality of the chest image samples; an inputting module configured to annotate feature points at lungs in the chest image samples and acquire contours of the lungs thereof; a processing module configured to perform a lung segmentation, including: pre-processing the chest image; acquiring a binary image of boundaries of a lung in the chest image; performing generalized Hough transform on the binary image to locate initial boundary of the lung to obtain a Hough location; aligning the lung model to the Hough location to obtain an alignment result; applying dynamic programming algorithm to the alignment result to obtain a segmentation result; and transforming the segmentation result back to a coordinate system of the chest image.

In some embodiments, the processing module is further configured to segment ribs based on the lung segmentation.

In some embodiments, the processing module is further configured to subtract the ribs from the lung.

In some embodiments, the outputting module displays the lung together with ribs, or displays the lung without the ribs.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
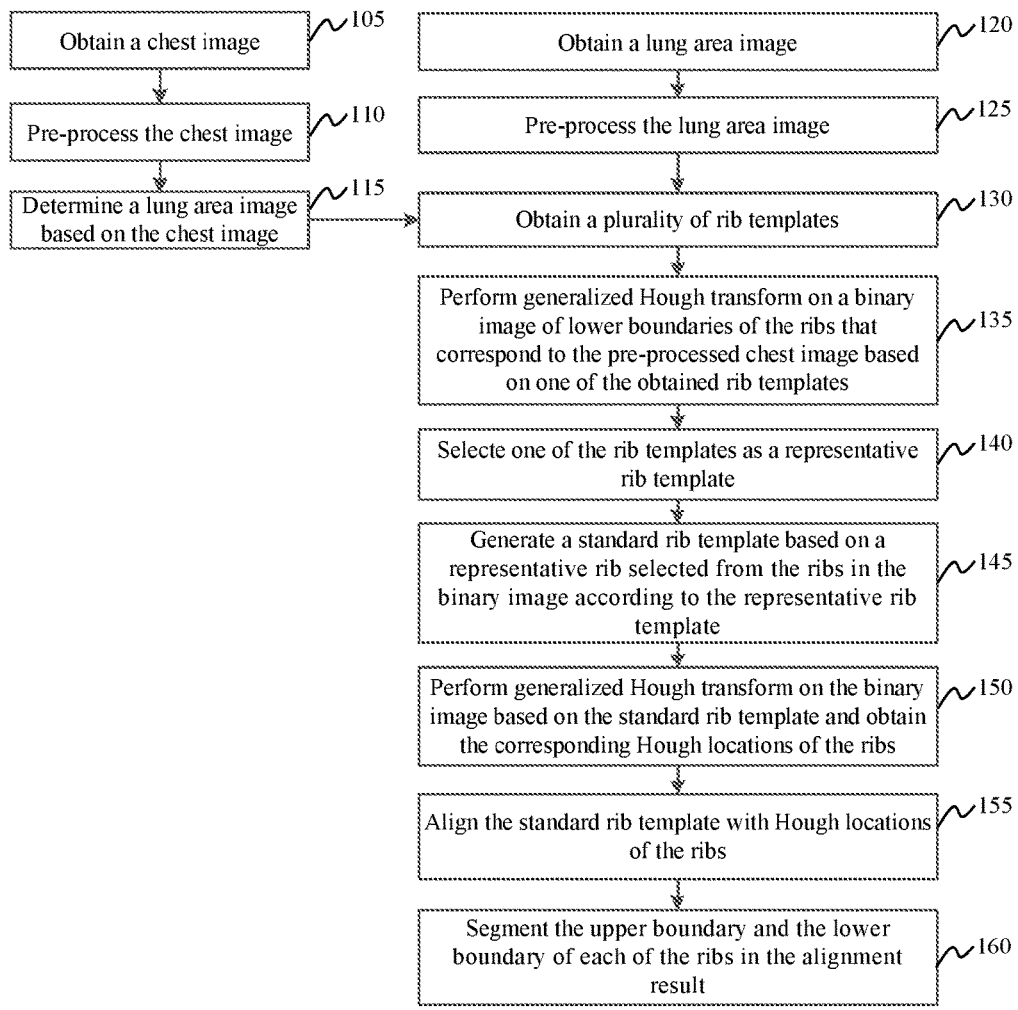
FIG. 1 illustrates a flowchart of an exemplary process for segmenting ribs in medical images according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "constructed" and "reconstruct", when used in this disclosure, may represent a similar process that an image may be transformed from data. It will be further understood that the terms "pixel" and "point" have similar meaning and are interchangeable, unless the context clearly indicates otherwise.

In some embodiments, the medical imaging system may be operated under various modalities, including but not limited to, Digital Subtraction Angiography (DSA), Magnetic Resonance Imaging (MM), Magnetic Resonance Angiography (MRA), Computed tomography (CT), Digital Radiography (DR), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transracial magnetic stimulation)-MR, US-CT, US-MR, X-ray-CT, X-ray-MR, X-ray-portal, X-ray-US, Video-CT, Vide-US, or the like, or any combination thereof. This is understood that the following descriptions are provided in connection with medical image processing for illustration purposes and not intended to limit the scope of the present disclosure. The image processing disclosed herein may be used for purposes other than medical treatment or diagnosis. For instance, the image processing may be used for purposes of detecting a fracture within a structure or its progression over time, a non-uniform portion within a piece of material, etc.

The radiation used by a medical imaging system may include a particle ray, a photon ray, or the like, or any combination thereof. The particle ray may include neutron, proton, electron, µ-meson, heavy ion, or the like, or any combination thereof. The photon beam may include X-ray, γ-ray, α-ray, β-ray, ultraviolet, laser, or the like, or any combination thereof.

For illustration purposes, the following description is provided to help better understanding an image processing. It is understood that this is not intended to limit the scope of the present disclosure. For persons having ordinary skills in the art, a certain amount of variations, changes and/or modifications may be deducted under guidance of the present disclosure. However, those variations, changes and/or modifications do not depart from the scope of the present disclosure.

The present disclosure provided herein relates to medical image processing. More specifically, the present disclosure relates to a system and method for segmenting lungs and/or ribs in digital chest radiographs (also referred to as chest images). The results of lungs and/or ribs segmentation may be widely used in diagnosis and treatment of patient.

FIG. 1 illustrates a flowchart of an exemplary process for segmenting ribs in a medical image according to some embodiments of the present disclosure. As shown in FIG. 1, the method of segmenting ribs in a medical image may include one or more of the following operations:

In 105, a chest image may be obtained. The chest image may include a portion corresponding to the chest of a subject, the lungs of the subject, and/or a portion corresponding to the ribs of the subject. Merely by way of example, the chest image may be acquired by a DR device/system or a CT device/system.

In 110, the chest image may be pre-processed. In some embodiments, the pre-processing may include, for example, de-noising, filtering, or the like, or any combination thereof.

In 115, a lung area image may be determined based on the chest image. The lung area image may include a portion corresponding to the left lung and/or the right lung of a subject, and/or a portion corresponding to the ribs of the subject. In some embodiments, the lung area image may include a portion corresponding to a segmented lung. The method of segmenting lung may be found elsewhere in the present disclosure. See, for example, FIGS. 7 and 8 and the description thereof.

In 120, a lung area image may be obtained. In some embodiments, the lung area image may be provided into the system by a user or a device.

In 125, the lung area image may be pre-processed. In some embodiments, the pre-processing may include, for example, de-noising, filtering, or the like, or any combination thereof.

In 130, a plurality of rib templates of Hough transform (also referred to as Hough templates) may be obtained. The rib templates may be automatically produced by a device with a drawing function, manually drawn by a user, or automatically or manually selected from a library including a plurality of templates that are pre-stored in a storing device or medium.

In 135, generalized Hough transform may be performed on a binary image of lower boundaries of the ribs that corresponds to the pre-processed chest image based on one of the obtained rib templates. The process for obtaining a binary image of lower boundaries of the ribs that corresponds to a pre-processed chest image may be found elsewhere in present disclosure. A maximum gravity value of the binary image based on that rib template may be obtained. The maximum gravity value may correspond to a point in the binary image and the point may be located at a rib which has highest similarity to the Hough template. This operation may be repeated for each of the rib templates to each generate a maximum gravity value of the binary image based on the respective rib template. Merely by way of example, the maximum gravity value, the point that corresponds to maximum gravity value or the rib at which the point is located based on different Hough templates may be different.

In 140, one of the rib templates may be selected as a representative rib template based on the maximum gravity values of the binary image. Merely by way of example, the rib template based on which the highest maximum gravity value of the binary image is obtained in the generalized Hough transform may be selected as the representative rib template.

In 145, a standard rib template may be generated based on a representative rib selected from the ribs in the binary image, according to the representative rib template. Merely by way of example, among the ribs included in the binary image, the rib that matches the representative rib template the best (that is, the rib in which the point of maximum gravity value is located) may be selected and designated as the representative rib. The standard rib template may be generated by way of thinning and interpolating the boundaries of the representative rib by, for example, curve fitting.

In 150, generalized Hough transform may be performed on the binary image based on the standard rib template to respectively locate the lower boundaries of the ribs and obtain the corresponding Hough locations of the ribs. For example, Hough location may be a location of the rib that includes the point of maximum gravity value in the binary image corresponding to the standard rib template. In some embodiments, lower boundaries of all the ribs in the binary image may be located. In some embodiments, lower boundaries of some ribs in the binary image may be located. In this case, the distance between adjacently located lower boundaries of ribs may be compared with a constrained dimension. In some embodiments, the constraint may include a pre-defined range. Merely by way of example, if the distance between two adjacent lower boundaries is in the range of the constrained dimension, these two adjacent lower boundaries may be considered to belong to two ribs located next to each other. If the distance between two adjacent lower boundaries exceeds the constrained dimension, it may be considered that there exist at least one additional rib between the two ribs; accordingly, further generalized Hough transform may be performed within the area between these two adjacent lower boundaries of the binary image to locate one or more unidentified ribs and identify the corresponding Hough location(s). If the distance between two adjacent lower boundaries is lower than the constrained dimension, one of the two adjacent lower boundaries may be considered an interfering subject and 150 may be performed again. It is understood that the conclusion whether two ribs are actually adjacent to each other may change if it is found out later that a criterion is not satisfied. For instance, if the distance between two "adjacent" ribs exceeds the constrained dimension, the two ribs may be considered not adjacent to each other. As another example, if the distance between two "adjacent ribs" is below the constrained dimension, it may be considered that one of the two "ribs" is inaccurately identified. It is understood that the "bottom boundary" and the "lower boundary" are used interchangeably and that the "top boundary" and the "upper boundary" are used interchangeably.

In 155, the standard rib template may be aligned with the Hough location of each of the ribs in the binary image to obtain an alignment result.

Figure 5:
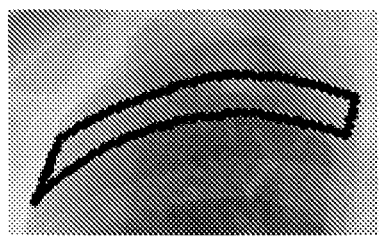
FIG. 5 illustrates an exemplary rib segmentation result transformed back to the original coordinate system according to some embodiments of the present disclosure.

In 160, the upper boundary and the lower boundary of each of the ribs in the alignment result may be segmented based on a bilateral dynamic programming algorithm to generate a segmentation result. The segmentation result may be transformed back to the original coordinate system (the coordinate system of the chest image), as illustrated in FIG. 5. Merely by way of example, 160 may include transforming the alignment result from a Cartesian coordinate system (original coordinate system) to a polar coordinate system before the alignment result is segmented. After the segmentation, the segmentation result obtained may be transformed back to the Cartesian coordinate system.

The aforementioned process may be executed by a plurality of computing devices, such as an imaging workstation, a CPU (central process unit), a DSP (Digital signal processor), a FPGA (Field Programmable Gate Array), a SCM (Single Chip Microcomputer), or the like, or any combination thereof. Those devices may be loaded or configured with software or programming for automatically searching, analyzing calculating, comparing, transforming data or values and outputting corresponding results.

In some embodiments, 105 through 115 and 120 through 125 may be alternatively performed. For example, the system may determine to perform 105 through 115 (rather than 120 through 125) before 130. As another example, the system may determine to perform 120 through 125 (rather than 105 through 115) before 130. In some embodiments, 130 may be performed before one of 105 through 115 and 120 through 125.

The chest image may be pre-processed by an image station or a computer. The pre-processing the chest image may include one or more of the following operations:

An original image may be acquired. The original image may be a human chest image including, for example, a DR image or an X-Ray image acquired by a DR device or an X-Ray device. The original image may be stored in a storing device or medium including, e.g. a hard driver disk (HDD), a compact disc (CD), or a cloud storage.

The original image may be filtered by a Gaussian filter to obtain a filtered image. In some embodiments, other type of filters, such as Butterworth filter, Chebyshev filter, Elliptic filter, Wiener filter, etc., may be used.

The filtered image may be subtracted from the original image to obtain a subtracted image.

An average gray scale of the filtered image may be added to the subtracted image to obtain a background removed image in which the background noise may be reduced or removed.

A bilateral filtering of the background removed image may be performed to obtain a pre-processed image.

The rib templates (or referred to as Hough templates) may be stored in a storing device or medium. As ribs may have different shapes, a plurality of Hough templates may be needed. The Hough templates may be obtained by analyzing a number of ribs in different medical images, and the edge shapes of representative ribs in the medical images may be chosen as the Hough templates. Alternatively, the Hough templates may be created automatically or drawn manually using a device with drawing functions or graphic tools.

Figure 2:
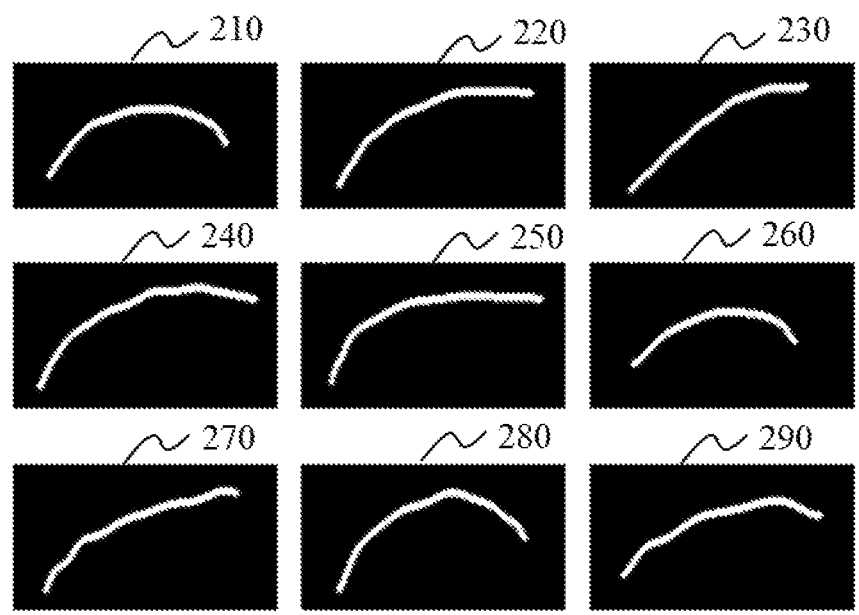
FIG. 2 illustrates exemplary rib templates according to some embodiments of the present disclosure.

FIG. 2 illustrates exemplary rib templates according to some embodiments of the present disclosure. As shown in FIG. 2, nine ribs with various shapes and angles may be used as the Hough templates 210, 220, 230, 240, 250, 260, 270, 280, and 290. It should be noted that the number of Hough templates is merely for illustration purposes and not intended to limit the scope of the present disclosure. A library may include a plurality of rib templates.

After the chest image (and/or lung area image) is pre-processed and the Hough templates are obtained, generalized Hough transform may be performed on the binary image of the lower boundaries of the ribs corresponding to the pre-processed chest image to obtain Hough locations based on the respective Hough templates, as described with reference to 135. Take one of the nine Hough templates 210 through 290 in FIG. 2 as an example. The upper section of the Hough template may be labelled. The coordinate of the gravity point of the Hough template and the coordinates of other points on the lower section of the Hough template with respect to the gravity point may be recorded. Then, generalized Hough transform may be performed to obtain a maximum gravity value of the binary image. In some embodiments, the maximum gravity value of the binary image may be obtained based on each of the remaining eight templates in a similar way.

In some embodiments, the generalized Hough transform may be used to find or verify the occurrence or location of a part (or referred to as locate the part) from a previously defined template in a target image. For example, the generalized Hough transform may be used to locate the lower or upper boundaries of a rib based on a previously defined Hough template in a chest image (or a binary image thereof).

The binary image may be generated by one or more of the following operations:

A boundary edge enhancement operator may be applied to the chest image to generate a gradient image in which the boundaries of the ribs may be enhanced, and a binary image may be obtained based on the gradient image. Merely by way of example, a Sobel edge enhancement filter may be used to enhance the lower boundaries of the ribs. Merely by way of example, the Sobel edge enhancement filter may generate a gradient image in which the value of every pixel is determined by subtracting the value of pixel at the same location in the chest image by the value of the pixel right next to it (e.g., the pixel above it if the value of a pixel on the upper boundary is to be obtained, or the pixel underneath it if the value of a pixel on the lower boundary is to be obtained). Merely by way of example, the value of a pixel may be the gray value of the pixel. Considering that the difference between the value of a pixel on the boundary (or referred to as an edge pixel) and the value of a pixel not on the boundary (or referred to as a non-edge pixel) next to the edge pixel may be higher than the difference between the values of two neighboring non-edge pixels, the values of edge pixels may be higher than the values of the non-edge pixels in the gradient image. The binary image corresponding to the chest image (or the pre-processed chest image) with the lower boundaries enhanced (or referred to as the binary image of the lower boundaries of ribs) may be produced by setting the values of the pixels of the highest values (e.g., highest 5%, or 8%, or 10%, or 12%, or 15%, or 18%, or 20%, etc.) in the gradient image as 1 (white) and the remaining pixels as 0 (black). In some embodiments, the values of the pixels located at a top section (e.g., a quarter of the height of the lung area) and a bottom section (e.g., a fifth of the height of the lung area) of the lung area in the produced binary image may be set to zero to remove or reduce the interference from a tissue or organ near the lung area or part of the lung area (e.g., the clavicle and lower end of the lung).

Figure 15A:
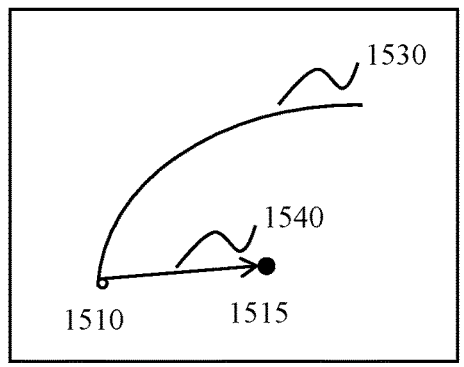
FIG. 15A, FIG. 15B, and FIG. 15C are exemplary diagrams of Hough transform according to some embodiments of the present disclosure.
Figure 15B:
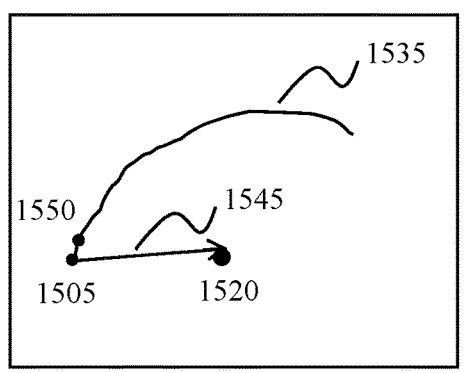
Figure 15C:
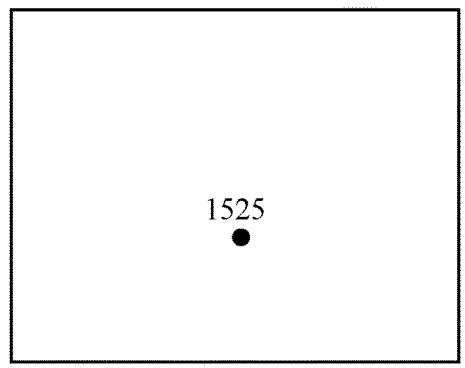

FIG. 15A, FIG. 15B, and FIG. 15C are exemplary diagrams of Hough transform according to some embodiments of the present disclosure. FIG. 15A illustrates an exemplary Hough template 1530. FIG. 15B illustrates an exemplary binary image of a boundary 1535. FIG. 15C illustrates a point in an exemplary image in the Hough space acquired as described below. Generalized Hough transform may include one or more of the following operations.

Each non-zero point in the binary image of the lower boundary of a rib may be used to match the Hough template. Merely by way of example, a non-zero point 1505 in the boundary 1535 may be used to match a point 1510 in the Hough template. The Hough template may contain a gravity point 1515 (e.g., a geometrical gravity point of the Hough template based on its shape), and a vector 1540 starting from the point 1510 to the gravity point 1515 may be obtained, as illustrated in FIG. 15A.

By generating a similar vector 1545 (a vector similar to the direction and length of the vector 1540) starting from the non-zero point 1505 in the binary image, the end point 1520 of vector may be obtained, as illustrated in FIG. 15B.

An empty image, in which the gravity values of all pixels are zero) in the Hough space, which may be an image of the same size as the binary image, may be generated, as illustrated in FIG. 15C.

A point 1525 in Hough space may be determined corresponding to the location of the point 1520. The gravity value of the point 1525 may be increased by one.

Similarly, point 1505 may be matched with each of the points in the Hough template 1530 to determine points in the binary image (similar to the point 1520 in the binary image). Corresponding points in the Hough space may be determined according to the points so determined in the binary image, and the gravity values of the corresponding points in the Hough space may be increased accordingly.

The same operations may be repeated by matching the non-zero point 1550 in the boundary 1535 to all the points in the Hough template 1530, and, an image in the Hough space may be obtained.

The rib that contains the point with the maximum value (gravity value) in the Hough space may be identified and the corresponding Hough location may be obtained and normalized. As used herein, a Hough location may refer to a location of the rib that includes the point of maximum gravity value.

The same operation may be repeated for each of other Hough templates to each generate a Hough location and a maximum gravity value based on the respective Hough template.

If nine Hough templates are used in Hough transform, nine Hough locations and nine gravity values may be acquired in the Hough space. Because the Hough templates may have different sizes, the gravity values of the Hough templates may be normalized, and then the Hough template based on which the highest maximum gravity value is obtained in the generalized Hough transformed may be selected as the representative rib template, as described with reference to 140.

In some embodiments, the ribs may have many different shapes, and nine or more Hough templates may be used to locate or match said different shapes of ribs in the binary image. After a representative rib template is obtained, a representative rib selected from the binary image of the lower boundaries of the ribs based on the representative rib template may be thinned and interpolated to form a standard rib template, as described with reference to 145.

Generalized Hough transform may then be performed on lower boundaries of the ribs in the binary image based on the standard rib template and Hough locations of the ribs in the binary image may be obtained, as described with reference to 150. The standard rib template may be aligned with the Hough locations to obtain an alignment result, as illustrated in 155.

In order to speed up the locating process, it may be assumed that the distance between adjacent ribs is similar or constant. As used herein, the distance between two ribs may be with respect to two ribs on the same side of the chest (e.g., two ribs both on the left side, or two ribs both on the right side). As used herein, the distance between two ribs may be the distance between the bottom edge of the rib located above the other rib and the bottom edge of the other rib. For example, the distance between two adjacent ribs may be assumed to be one tenth of the lung height in the chest image (or the pre-processed chest image). The distance between two adjacent ribs may be compared with a constrain dimension as described in 150. It is understand that the conclusion whether two ribs are actually adjacent to each other may change based on the comparison. Merely by way of example, the constrained dimension may be the range from eleven to twenty pixels. The ribs on either the right side or the left side may be located by the same approach and the alignment result may be obtained accordingly.

Figure 3:
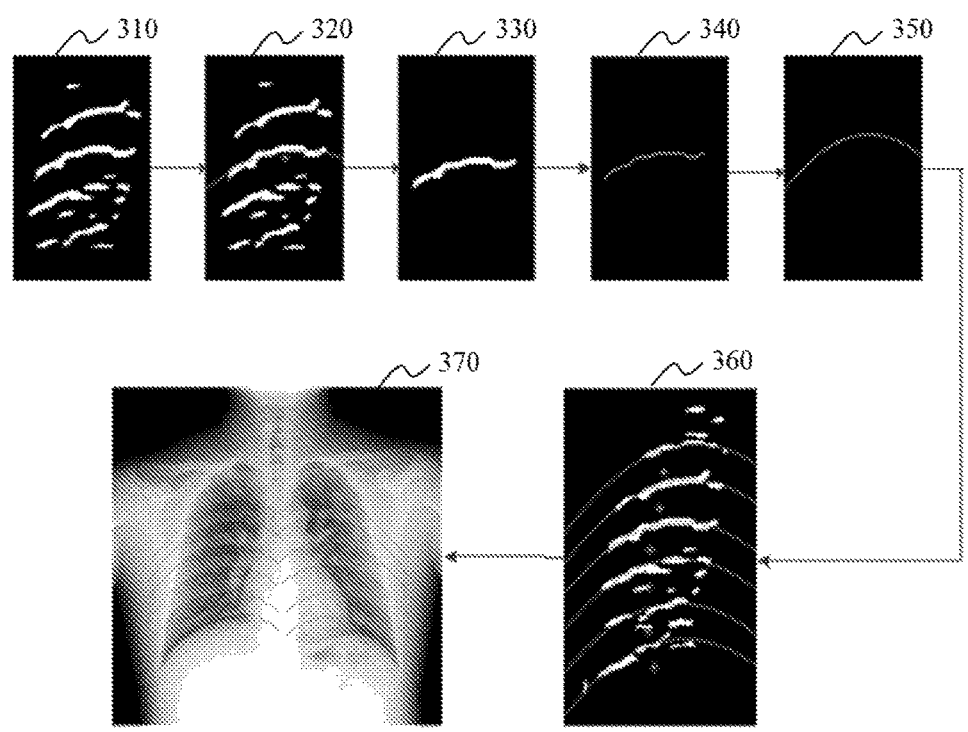
FIG. 3 illustrates exemplary diagrams of locating lower boundaries of the ribs according to some embodiments of the present disclosure.

FIG. 3 illustrates exemplary diagrams of locating the lower boundaries of the ribs according to some embodiments of the present disclosure. Image 310 illustrates a binary image of lower boundaries of several ribs in a right lung. Image 310 may be generated from a chest image (or a pre-processed chest image) according to the description elsewhere in present disclosure. Image 320 illustrates a representative rib located by performing Hough transform. Image 330 illustrates the representative rib located and selected from the ribs in image 320. Image 340 illustrates a rib generated by thinning the representative rib in image 330. Image 350 illustrates a standard rib template generated by interpolating the thinned rib in image 340. Image 360 illustrates an alignment result of the right lung generated by performing Hough transform on image 310 based on the standard rib template. Image 370 illustrates the segmentation result of the lower boundaries of the ribs in a chest image.

After the alignment result is obtained, a bilateral dynamic programming algorithm may be applied to the alignment result to obtain a segmentation result. In some embodiments, the upper and lower boundaries of a rib may be approximately parallel and the thickness of the ribs in a chest image (or a pre-processed chest image) may be similar. Therefore, the shape and location of upper boundaries of each rib within the lung area may be estimated based on the located lower boundaries of ribs. For example, a segmentation result may be obtained by employing a bilateral dynamic programming algorithm based on the alignment result and the located lower boundaries of ribs. For analyzing chest images (or pre-processed chest images) of different people, different Hough templates may be identified as representative Hough templates. Differences in the ribs of different people may be further reflected in respective standard rib templates obtained as described.

Figure 4A:
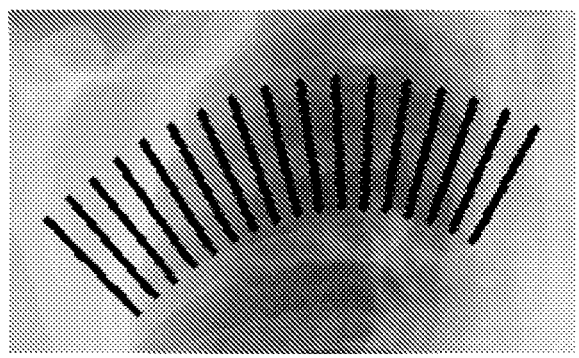
FIG. 4A and FIG. 4B illustrate exemplary diagrams of acquiring a normal matrix related to the lower boundaries of the ribs according to some embodiments of the present disclosure.
Figure 4B:
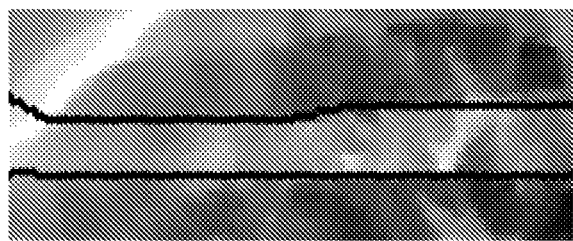

In some embodiments, straight lines, as illustrated in FIG. 4A, may be generated by passing through each point on the lower boundary such that each line is normal (or substantially normal) to the lower boundary of a rib. Such a straight line may also be referred to as a normal line. Pixels on these normal lines may be rearranged into columns to form a two-dimensional image as shown in FIG. 4B. After the rearrangement, the rib may become nearly a horizontal band (also referred to as a transformed image) and the lower boundary of the rib may be expressed as a normal matrix. The bilateral dynamic programming algorithm may be employed, and the width of the ribs and the smoothness of the rib boundaries may be included in the cost function of the bilateral dynamic programming algorithm, to generate a segmentation result of the two nearly parallel boundaries of the horizontal band, which may represent the upper and lower boundaries of the rib, respectively. Finally, the two boundaries may be rearranged or mapped back into the lung area of the original image to form the two boundaries of the rib. It should be noted that the bilateral dynamic programming algorithm may be executed by a computer, a SCM, a FPGA, etc.

In some embodiments, the cost function may include an internal cost function and an external cost function. Unlike the classic algorithm, the dynamic programming algorithm may be modified to include a constrained parameter d.

The internal cost function $E_{int}$ may be defined as:

$$E_{int}(i, j, d) = \quad (1)$$
$$\alpha \times \frac{|k-j|}{k+j} + \beta \times \frac{|d_k - d_j|}{d_k + d_j} + \gamma \times \frac{|(k-d_k)-(j-d_j)|}{(k-d_k)} + (j-d_j),$$
$$d_j = d_k - B, \ldots, d_k + B, j = 1, \ldots, m,$$
$$k = j - B, \ldots, j + B, i > 1,$$

where i and j may denote the x-coordinate and the y-coordinate of the ith edge point, k may denote the y-coordinates of the edge point on the (i−1)th column of the transformed image/normal matrix, m and n may denote the width and the height of the transformed image, respectively, d may denote the width of a rib, $d_j$ and $d_k$ may denote the width of rib at the ith and (i−1)th columns, respectively, (for example, $d_j$ and $d_k$ may take values in the range from eleven to twenty pixels), and α, β, and γ may denote the weighting factors for three terms, respectively. B may be an integer greater than 1.

In some embodiments, the terms in formula (1) may be normalized. In some embodiments, the smoothness of the boundary may relate to the value of the internal cost. In some embodiments, a lower internal cost may indicate a smoother boundary.

The external cost function $E_{ext}$ which represents the edge strength at each point may be defined as:

$$E_{ext}(i,j,d) = -(\omega_{down} \times g_1(i,j) + \omega_{up} \times g_2(i,j-d)), d=11 \ldots 20, \quad (2)$$

where i and j may denote the x-coordinate and the y-coordinate of the ith edge point, and $\omega_{up}$ and $\omega_{down}$ may denote weighting factors.

The upper boundary and the lower boundary of a rib may be simultaneously searched, and gradient images of the normal matrix may include a lower boundary gradient $g_1(i,j)$ and an upper boundary gradient $g_2(i,j-d)$. The constrained parameter d may be used to control the searching range of the upper boundary. Merely by way of example, d may have a value in the range from eleven to twenty pixels.

The local cost function E, which may relate to the internal cost function $E_{int}$ and the external cost function $E_{ext}$, may be defined as:

$$E(i,j,d)=\omega_{int} \times E_{int}(i,j,d)+\omega_{ext} \times E_{ext}(i,j,d), \quad (3)$$

where $\omega_{int}$ and $\omega_{ext}$ may denote the weighting factors. Merely by way of example, $\omega_{up}=0.7$, $\omega_{down}=0.3$, $\omega_{int}=1.9$, and $\omega_{ext}=2.4$.

In some embodiments, cumulative cost of a current column in the normal matrix may be the cumulative cost of the previous column plus the local cost of the current column. The cumulative cost may be defined as:

$$\begin{cases} \text{Cost}(1, j, d) = \min_{d} E_{ext}(1, j, d) \\ \text{Cost}(i, j, d) = \min_{\substack{j-3 \leq k \leq j+3 \\ d}} \{\text{Cost}(i-1, k, d) + E(i, j, d)\} \end{cases} \quad (4)$$

where k may denote the searching range of (i−1)th column, and d may denote the width of the rib. The value of k and d may be stored in a matrix D, while the cumulative cost of the current column may be determined based on matrix D. As the first column has no internal cost, the cumulative cost of the first column may equal to its external cost.

In some embodiments, an optimal searching path, which corresponds to an optimal segmentation result, may be obtained. The method of obtaining the optimal searching path may include one or more of the following operations:

The minimum cumulative cost of the last column, regarding the corresponding k and d, may be obtained. In some embodiments, the minimum cumulative cost may be set as an initial point.

The normal matrix according to k and d of other cumulative cost of previous columns may be forwardly traced.

The optimal path on the lower boundary of the rib may be obtained, and the optimal path on the upper boundary of the rib may be obtained based on d.

The optimal paths on the lower boundaries and/or the upper boundaries may be transformed back to the original coordinate system from the Hough space to obtain a segmentation result.

FIG. 5 illustrates an exemplary rib segmentation result transformed back to the original coordinate system according to some embodiments of the present disclosure. The rib as illustrated in FIG. 5 may be generated by segmenting corresponding rib in the chest image using the bilateral dynamic programming algorithm as described elsewhere in the present disclosure.

Figure 6:
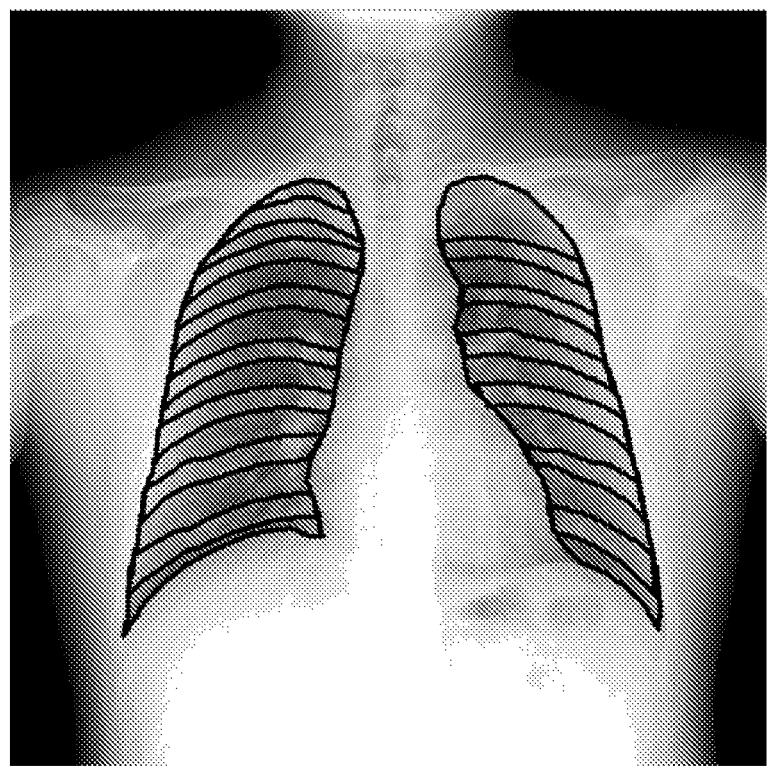
FIG. 6 illustrates an exemplary ribs segmentation in lungs according to some embodiments of the present disclosure.

FIG. 6 illustrates an exemplary ribs segmentation in lung areas in a chest image according to some embodiments of the present disclosure. In some embodiments, the ribs shown in FIG. 6 may be segmented using the bilateral dynamic programming algorithm as described elsewhere in the present disclosure. In some embodiments, before rib segmentation, one or more lung areas (left lung area and/or right lung area) in a chest image as marked in FIG. 6 may be segmented.

Figure 16:
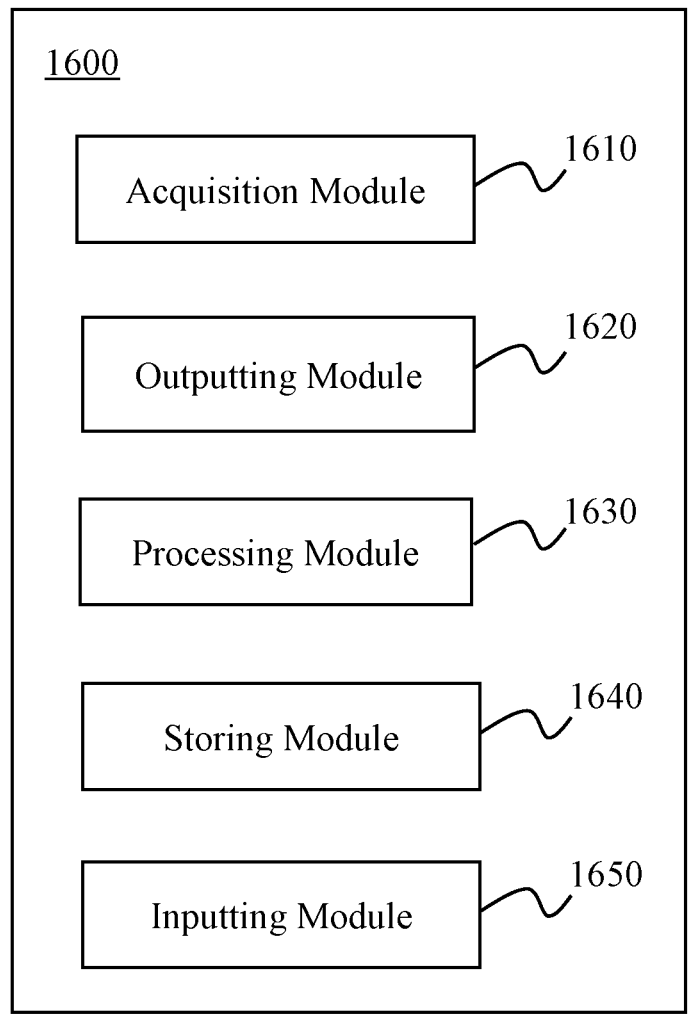
FIG. 16 is an exemplary block diagram of an image segmentation system according to some embodiments of the present disclosure.

Referring to FIG. 16, an image segmentation system may include an acquisition module 1610, an outputting module 1620, a processing module 1630, a storing module 1640, and an inputting module 1650.

The storing module 1640 may be configured to store at least a chest image and a plurality of rib templates of generalized Hough transform.

The outputting module 1620 may be configured to display at least an image.

The processing module 1630 may be configured to:
obtain the chest image including a plurality of ribs;
obtain the plurality of rib templates;
pre-process the chest image;
generating a binary image of lower boundaries of the ribs based on the pre-processed image;
perform generalized Hough transform on the binary and obtain maximum gravity value based on the rib templates;
select one of the Hough templates as a representative rib template based on the gravity values;
generate a standard rib template based on a representative rib selected from the ribs in the binary image according to the representative rib template, wherein standard rib template may be generated by way of thinning and/or interpolating the representative rib by, for example, curve fitting;
perform a generalized Hough transform on the binary image based on the standard rib template to respectively locate the lower boundaries of the ribs and obtain the corresponding Hough locations of the ribs;
align the standard rib template with the Hough locations of the ribs to obtain an alignment result;
segment the upper and lower boundaries of the ribs in the alignment result based on a bilateral dynamic programming algorithm to generate a segmentation result; and
transform the segmentation result back to the coordinate system of the chest image.

Furthermore, the processing module 1630 may be configured to segment a lung in the chest image and remove the ribs out of the chest image. The outputting module 1620 may be configured to display the segmented chest image of the lung without ribs inside.

The processing module 1630 may transfer the information from the storage module to a particular form that may be identified, understood, or executed by the processing module 1630. The processing module 1630 may process the information from an acquisition module 1610 to retrieve data from the storage module. The information transfer from the acquisition module 1610 to the output module may be processed by the processing module 1630 so that it may be identified, understood, or executed by the processing module 1630. The above description of the processing module 1630 is merely for exemplary purposes, should not be understood as the only embodiments, and these examples do not limit the scope of the present disclosure.

In some embodiments, the processing module 1630 may be implemented on a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an Advanced RISC Machines (ARM), or the like, or any combination thereof.

The storage module may store information related to image processing. In some embodiments, the storage module may perform storage-related functions, such as data consolidation and/or data pre-processing. The storage module may acquire information from or output information to other modules. Merely by way of example, the storage module may receive the data from the acquisition module 1610, and then convey it to the processing module 1630, optionally after pre-processing the data. The information stored in the storage module may be acquired from or output to an external resource, such as a floppy disk, a hard disk, a CD-ROM, a network server, a cloud server, a wireless terminal, or the like, or any combination thereof.

The system for segmenting ribs in a medical image may further include an inputting module 1650. The inputting module 1650 may be implemented on, connected to or communicate with a peripheral device that may provide data and/or control signals to the processing module 1630 and/or the storage module. For instance, the inputting module 1650 may include an input device such as a keyboard, a mouse, a scanner, a digital camera, a joystick, a touch screen, or the like, or a combination thereof.

The outputting module 1620 may be implemented on a computer or a device that may output the results of the image processing obtained in the processing module 1630. In some embodiments, the outputting module 1620 may convert the electronically generated information into a human-readable format. For example, the outputting module 1620 may include a display device such as a CRT monitors, a LCD monitor, a display, a gas plasma monitor, a television, etc.

Figure 7:
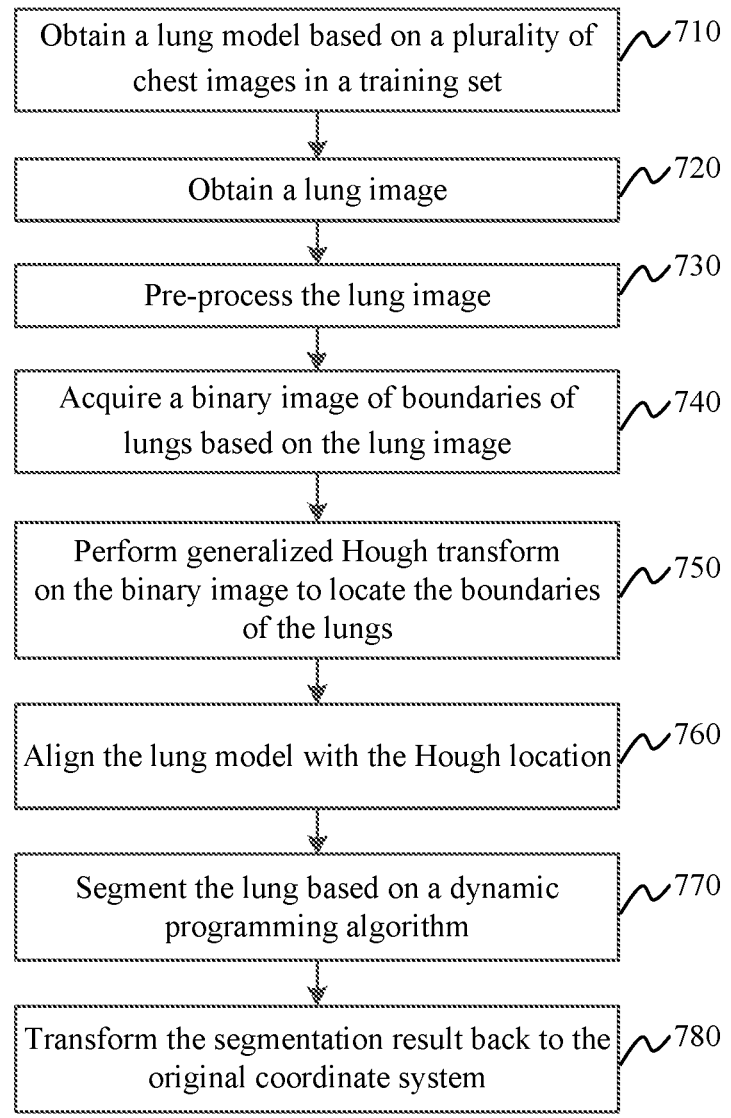
FIG. 7 illustrates a flowchart of an exemplary process for segmenting a lung in a medical image according to some embodiments of the present disclosure.

FIG. 7 illustrates a flowchart of an exemplary process for segmenting a lung in a medical image according to some embodiments of the present disclosure. As shown in FIG. 7, the method of segmenting a lung in medical images may include one or more of the following operations.

In 710, a lung model may be obtained based on a plurality of chest image samples in a training set. An exemplary process for obtaining the lung model may be found in FIG. 9A and FIG. 9B and the description thereof.

In 720, a lung image may be obtained. In some embodiments, the lung image may be pre-processed in 730.

In 740, a binary image of boundaries of lungs may be acquired based on the lung image. Merely by way of example, a boundary edge enhancement operator (e.g. a Sobel edge enhancement filter) may be applied to the edge profile of the lung image to generate a gradient image in which the edge profile is enhanced, and a binary image corresponding to the edge profile of the lung image may be obtained. As used herein, an edge profile of the lung image may include the contour of a lung in the lung image. If a lung image shows two lungs, the lung image may include two edge profiles. An exemplary process for obtaining the binary image may be found elsewhere in present disclosure.

In 750, generalized Hough transform may be performed on the binary image to locate the boundaries of the lungs based on lung templates, and Hough locations of the boundaries may be obtained. Merely by way of example, each non-zero point of the edge profile may be used to match the points of the lung in one or more lung templates. In some embodiments, a lung template may correspond to a section of the contour of a lung (or referred to as a lung contour), and the entire contour of the lung may correspond to a plurality of lung templates. For instance, the entire contour of a lung may correspond to a lung template with respect to the left edge of the lung, a lung template with respect to the right edge of the lung, a lung template with respect to the upper edge of the lung, and a lung template with respect to the lower edge of the lung. The left edge or the right edge may be referred to as a lateral edge. Similarly, an edge profile corresponding to a lung may include sections. A section of the edge profile may be matched with a lung template. An exemplary process for matching the points and obtaining gravity value of the points of the edge profile (or a section thereof) may be found elsewhere in present disclosure. After matching all the non-zero points of the edge profile (or a section thereof) in the binary image with the points of the lung template, an image in the Hough space, which may be of the same size as the binary image may be obtained. The point with the maximum value (gravity value) in the Hough space may be identified and normalized as the Hough locations corresponding to that particular lung template.

If the edge profile of a lung includes a plurality sections, the process may be repeated based on different lung templates corresponding to different sections of the edge profile. Various Hough locations corresponding to different sections of the edge profile may be obtained. These Hough locations may be combined to form a Hough location of the edge profile. The edge profile corresponding to the left lung and the edge profile corresponding to the right lung may be processed similarly.

In 760, the lung model may be aligned with the Hough location to obtain an alignment result.

In 770, a dynamic programming algorithm may be applied to the alignment result to obtain a segmentation result.

In 780, the segmentation result may be transformed back to the original coordinate system of the chest image.

In some embodiments, the lungs segmentation may be executed by, for example, a computer (e.g., a processing module implemented on the computer) as described elsewhere in the present disclosure. The dynamic programming algorithm employed for lung segmentation may include obtaining local cost, calculating cumulative cost, and/or backwardly searching optimal path. Merely by way of example, 770 may include transforming the alignment result from a Cartesian coordinate system (original coordinate system) to a polar coordinate system before the alignment result is segmented. After the segmentation, the segmentation result obtained may be transformed back to the Cartesian coordinate system in 780.

The local cost may include an internal cost and an external cost. The internal cost may represent the smoothness of a boundary in an image. The external cost may represent the gradient of the change of intensity of pixels in the image.

If the size of the normal matrix is m*n, then the internal cost function may be expressed as:

$$E_{int}(i,j)=|j-k|/(j+k), j=1 \ldots n, k=1 \ldots n, i=1 \ldots m, \qquad (5)$$

where n may denote length of the lung template, m may denote height of the pixel value of the feature points along the normal direction, and j and k may denote pixel values of the feature points of ith column and (i−1)th column of the normal matrix respectively. In some embodiments, the terms in formula (5) may be normalized.

The external cost may be expressed as a negative value of a gradient image of the normal matrix as following:

$$E_{ext}(i,j)=-G(i,j). \qquad (6)$$

The local cost, which relates to the internal cost and the external cost may be expressed as:

$$E(i,j)=\omega_{int} \times E_{int}(i,j)+\omega_{ext} \times E_{ext}(i,j), \qquad (7)$$

where $\omega_{int}$, $\omega_{ext}$ may denote weight factors for internal cost and external cost, respectively.

Cumulative cost of current column in the normal matrix may be the cumulative cost of previous column plus the local cost of current column, and the cumulative cost may be expressed as:

$$\begin{cases} \text{Cost}(1, j) = E_{ext}(1, j) \\ \text{Cost}(i, j) = \min_{j-3 \leq k \leq j+3} \{\text{Cost}(i-1, k) + E(i, j)\}, i = 2 \ldots n \end{cases} \quad (8)$$

where the parameter k may denote the searching range of (i−1)th column, and the pixel size of two adjacent columns may be restrained. The value of parameter k is recorded, while the cumulative cost of the corresponding column is determined. As the first column has no internal cost, the cumulative cost of the first column is equal to its external cost.

In some embodiments, an optimal searching path, which corresponds to an optimal segmentation result, may be obtained. The process for obtaining the optimal searching path may include one or more of the following operations.

The minimum cumulative cost of the last column, regarding the corresponding k and d, may be obtained. In some embodiments, the minimum cumulative cost may be set as an initial point.

The cumulative cost of each of the previous columns may be forwardly traced according to k. The optimal path may be obtained. The optimal path may be transformed back to the original coordinate system from the Hough space to obtain a segmentation result.

Figure 8:
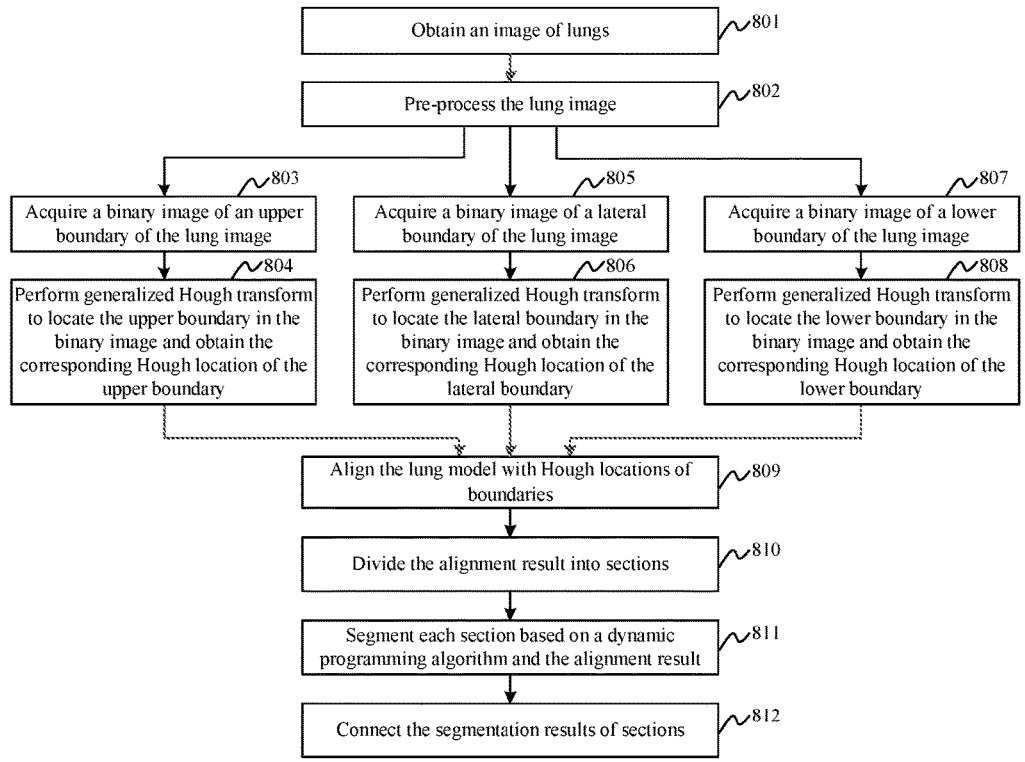
FIG. 8 illustrates a flowchart of an exemplary process for segmenting a lung in a medical image according to some embodiments of the present disclosure.

FIG. 8 illustrates a flowchart of an exemplary process for segmenting a lung in a medical image according to some embodiments of the present disclosure. An image including a portion reflecting or corresponding to a tissue or organ (e.g., a lung, a rib) may be referred to as, for brevity, an image of the tissue or organ. Similarly, segmenting a portion reflecting a tissue or organ (e.g., a lung, a rib) from an image may be referred to as, for brevity, segmenting the tissue or organ from the image or a transformed form thereof. As shown in FIG. 8, the process for segmenting the lung model may include one or more of the following operations.

In 801, an image of lungs (or referred to as a lung image) may be obtained in a chest image.

In 802, the lung image or the chest image may be pre-processed, as described elsewhere in the present disclosure. See, for example, FIG. 1 and the descriptions thereof.

In 803, 805, and 807, binary images of the upper boundary, the lower boundary, and lateral boundaries (that together may form a lung contour) of the lung may be acquired, respectively. The approach to generate a binary image may be found elsewhere in present disclosure.

In 804, 806, and 808, generalized Hough transform may be performed to locate the upper boundary, the lower boundary, and lateral boundaries in the binary images, respectively, based on a plurality of lung templates, and the Hough locations corresponding to the boundaries may be obtained accordingly. In some embodiments, the plurality of lung templates may be obtained based on shape of the lung contour. In some embodiments, a plurality of generalized Hough transform may be performed based on the plurality of lung templates and a plurality of maximum gravity values may be obtained for each lung template. One of the plurality of lung templates may be selected as a representative lung template for each binary image based on the respective maximum gravity values. The process for selecting the representative lung template and obtaining the Hough location may be similar to that described in 135 of FIG. 1. Merely by way of example, three to eight lung templates may be obtained. As another example, five lung templates may be obtained (for example, the shapes and size of the five lung templates may be shown as lung template 1010, 1020, 1030, 1040, and 1050 in FIG. 10).

In 809, the lung model may be aligned with the Hough locations of boundaries to obtain an alignment result.

In 810, the alignment result may be divided into a number of sections, e.g., the upper section, the lower section, and the lateral sections.

Figure 13:
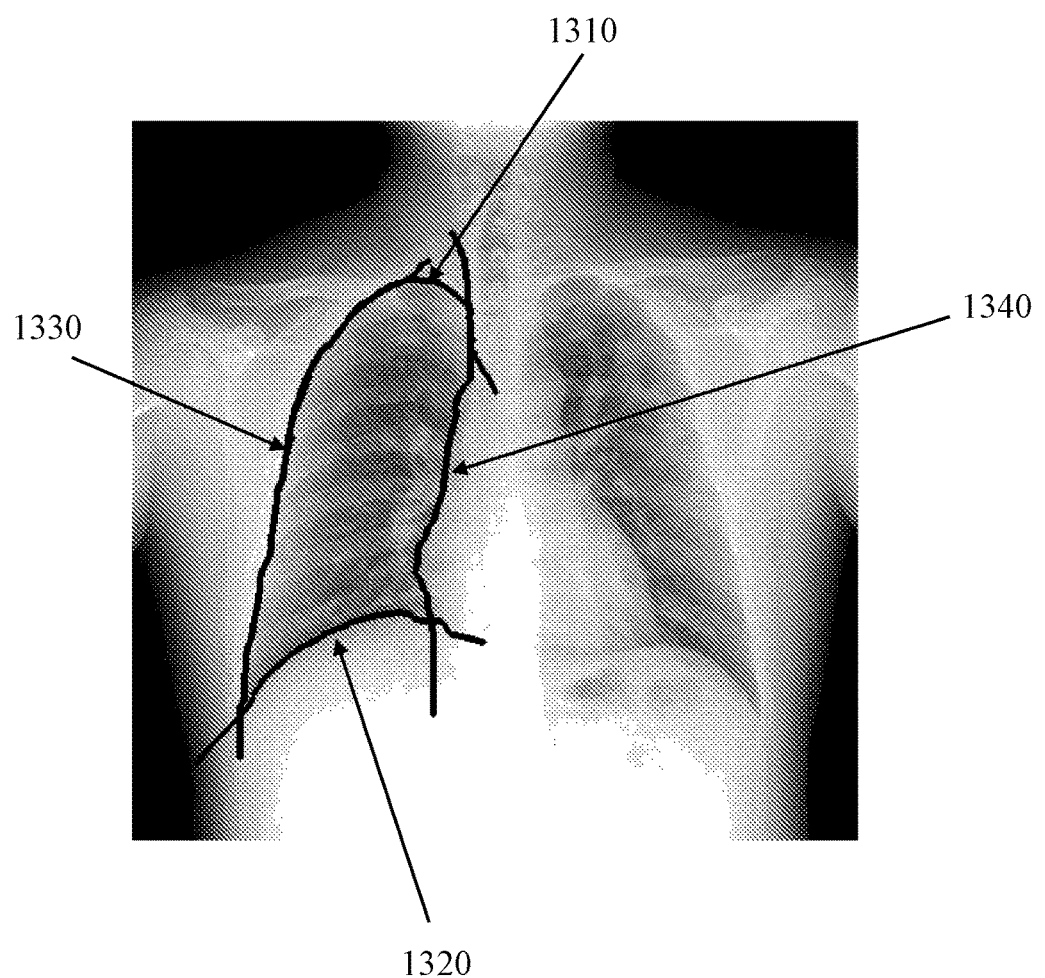
FIG. 13 is an exemplary diagram of a preliminary lung segmentation according to some embodiments of the present disclosure.

In 811, dynamic programming algorithm may be employed to segment each section based on the alignment result, and the segmentation result of each section may be obtained. An exemplary result of the segmentation result is shown in FIG. 13.

In 812, the segmentation results of the sections may be connected together to generate a segmentation result of the whole lung (final segmentation result).

The lung image may be pre-processed by an image station or a computer. The pre-processing of the chest image may include one or more of the following operations.

An original image may be acquired. The original image may be a human chest image including, for example, a DR image or an X-Ray image acquired by a corresponding DR device or X-Ray device. The original image may be stored in a storing device or medium including, e.g. a hard driver disk (HDD), a compact disc (CD), or a cloud storage. The original image may include at least a portion of a lung. The original image may be filtered by a Gaussian filter to obtain a filtered image. The filtered image may be subtracted from the original image to obtain a subtracted image. An average gray scale of the filtered image may be added to the subtracted image to obtain a background removed image in which the background noise may be reduced or removed. A bilateral filtering on the background removed image may be performed to obtain a pre-processed image.

Figure 9A:
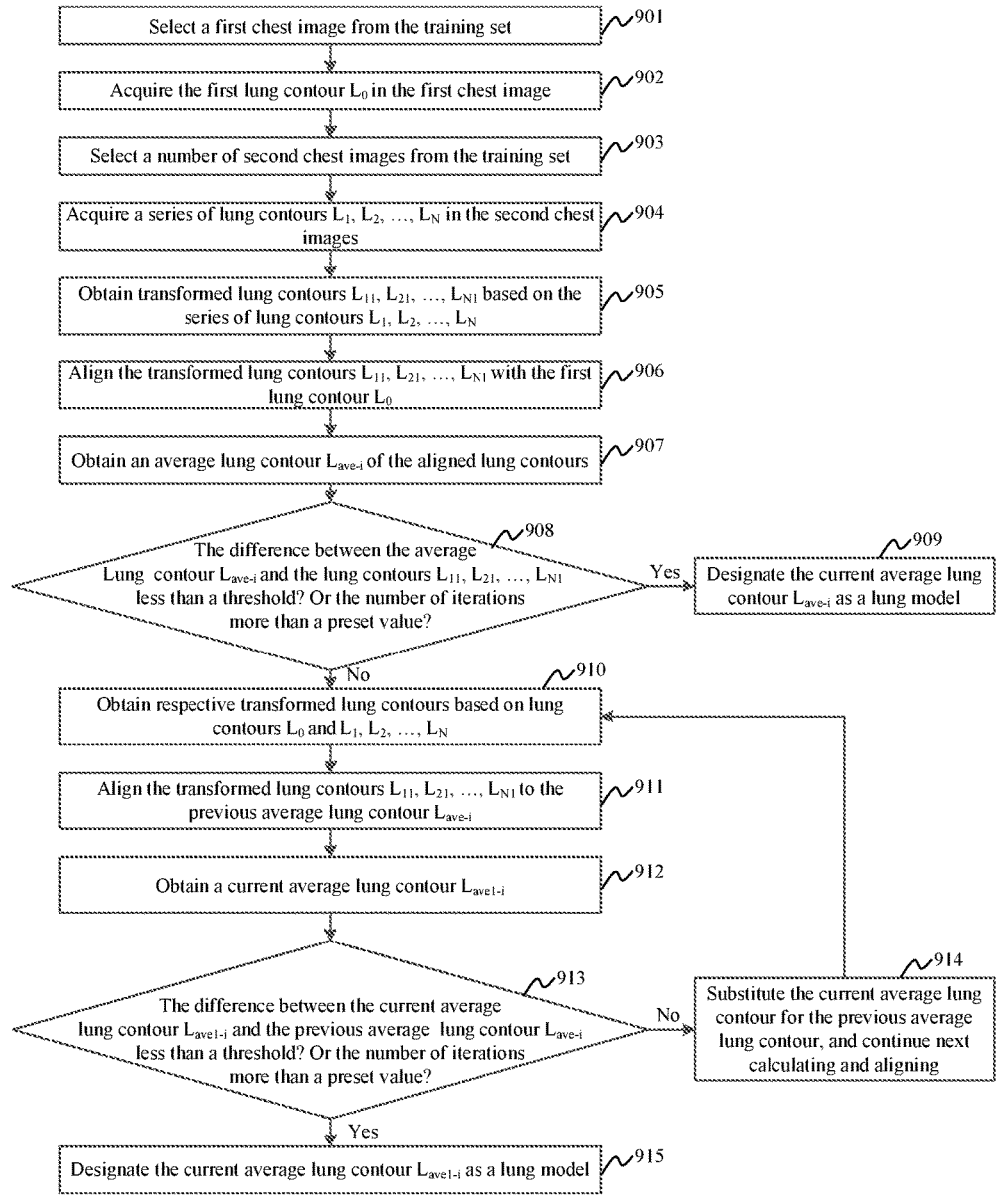
FIG. 9A illustrates a flowchart of an exemplary process for obtaining a lung model according to some embodiments of the present disclosure.

FIG. 9A illustrates a flowchart of an exemplary process for obtaining a lung model according to some embodiments of the present disclosure.

In 901, a first chest image sample may be selected from a training set. The training set may include a plurality of chest image samples pre-acquired by an acquisition module 1610. The acquisition module 1610 may include a digital radiograph device, a CT device, an MR device, etc. In some embodiments, the chest image samples may be stored in a storing module 1640. Merely by way of example, the number of chest image samples in the training set may be, e.g., ten, twenty, thirty, fifty, eighty, a hundred, a hundred and twenty, a hundred and fifty, or other numbers. Each of the chest image samples may have a pair of lungs therein. A plurality of lung templates may be manually created according to the contours (also referred to as upper, lower, and lateral boundaries or section) of the lungs in a chest image sample previously obtained. In some embodiments, the number of the lung templates corresponding to a lung may be in the range from three to eight or more. Merely by way of example, five lung templates may be created with respect to a lung. Furthermore, each lung template may correspond to an upper section, a lower section, or a lateral section.

Several chest image samples of the training set may be pre-processed. For example, M chest image samples may be randomly chosen from the training set, where M is an integer. Merely by way of example, M may be forty-two. Moreover, lungs in each chest image sample may be annotated by the same number of feature points such that the contour or the boundaries of the lung may be delineated by the feature points. The feature points on the lungs in the different chest image samples may be annotated at similar locations. Merely by way of example, the feature points may be annotated at the corners, the highest point, the lowest point, and any other points on the contour of each lung. In addition, the feature points on the contour of each lung except for those at the corners, the highest point, and the lowest point may be equally spaced.

In 902, a first lung contour (reference lung contour) $L_0$ in the selected chest image sample may be acquired. $L_0$ may be an array storing data of the lung contour (e.g. coordinate of the pixels in the lung contour).

In 903, a plurality of second chest image samples may be selected from the training set.

In 904, a series of lung contours $L_1, L_2, \ldots, L_N$ in the second chest image samples may be acquired. $L_1, L_2, \ldots, L_N$ may include arrays storing data (e.g. coordinate of the pixels) of the lung contours, respectively. It should be noted that the number of the lung contours acquired in 904 is merely for illustration purposes and not intended to limit the scope of the present disclosure. For example, one lung contour $L_1$ in a second chest image sample may be acquired.

In 905, the series of lung contours $L_1, L_2, \ldots, L_N$ may be processed to obtain transformed (corrected) lung contours $L_{11}, L_{21}, \ldots, L_{N1}$. The processing of the series of lung contours may include rotation, scaling, and translation transformations.

In 906, the transformed (corrected) lung contours $L_{11}, L_{21}, \ldots, L_{N1}$ may be aligned with the first lung contour $L_0$. For example, the gravity point of each of the transformed (corrected) lung contours $L_{11}, L_{21}, \ldots, L_{N1}$ may be aligned with the gravity point of the first lung contour $L_0$. The alignment of the gravity points may facilitate the alignment of the transformed (corrected) lung contours $L_{11}, L_{21}, \ldots, L_{N1}$.

In 907, an average lung contour $L_{ave-i}$ may be obtained based on the first lung contour $L_0$ and the transformed (corrected) lung contours $L_{11}, L_{21}, \ldots, L_{N1}$ Merely by way of example, coordinates of a pixel in the average lung contour $L_{ave-i}$ may be obtained by taking an average of coordinates of a corresponding pixel in the first lung contour $L_0$ and the transformed (corrected) lung contours $L_{11}, L_{21}, \ldots, L_{N1}$.

In 908, the average lung contour $L_{ave-i}$ obtained in the current round of iteration (or referred to as the current average lung contour) and the lung contours $L_{11}, L_{21}, \ldots, L_{N1}$ may be compared to get a difference. An assessment may be made as to whether a lung model is obtained. For instance, the difference may be compared with a threshold or the number of iterations may be compared with a pre-set value. If the difference is less than the threshold or the number of iterations exceeds the pre-set value, the current average lung contour $L_{ave-i}$ may be designated as a lung model in 909; otherwise, the process may proceed to 910.

In 910, all lung contours (including the first lung $L_0$ and the series of lung contours $L_1, L_2, \ldots, L_N$) may be processed to obtain respective transformed (corrected) lung contours. The processing of the series of lung contours may include:
performing rotation, scaling, and/or translation transformation on the first lung contour $L_0$ with respect to the previous average lung contour $L_{ave-i}$ to obtain a transformed (corrected) first lung contour $L_{0i}$; and
performing rotation, scaling, and/or translation transformation on the series of lung contours $L_{11}, L_{21}, \ldots, L_{N1}$ with respect to the average lung contour $L_{ave-i}$ acquired in the previous round of iteration (or referred to as a previous average lung contour) to obtain transformed (corrected) lung contours $L_{1i}, L_{2i}, \ldots, L_{Ni}$. As used herein, "current" may indicate a result in an iteration, while "previous" may indicate a result in a preceding round of iteration. For instance, a current average lung contour may refer to an average lung contour obtained in a current round of iteration, while a previous average lung contour may refer to an average lung contour obtained in the iteration that precedes the current round iteration.

In 911, the transformed (corrected) lung contours $L_{11}, L_{21}, \ldots, L_{N1}$ may be aligned with the previous average lung contour $L_{ave-i}$.

In 912, the current average lung contour $L_{ave1-i}$ may be obtained.

In 913, the current average lung contour $L_{ave1-i}$ and the previous average lung contour $L_{ave-i}$ may be compared to get a difference. An assessment may be made as to whether a lung model is obtained. For instance, the difference may be compared with a threshold and/or the number of iterations may be compared with a pre-set value. If the difference is less than the threshold and/or the number of iterations is more than the pre-set value, the current average lung contour $L_{ave1-i}$ may be designated as a lung model in 915; otherwise, the process may proceed to 914.

In 914, one or more of the following operations may be performed:
the current average lung contour $L_{ave1-i}$ may be assigned the value of the previous average lung contour $L_{ave-i}$;
the transformed first contour $L_{0i}$ may be designated as the first lung contour $L_0$;
the transformed (corrected) contours $L_{11}, L_{2i}, \ldots, L_{Ni}$ may be designated as the contours $L_{11}, L_{21}, \ldots, L_{N1}$, respectively;
the value of i may be increased by 1, and
the process may proceed to 910.

The parameter i may be an integer greater than 1, $L_{1i}, L_{2i}, \ldots, L_{Ni}$ and $L_{ave-i}$ may be arrays storing data (e.g., coordinates of pixels) of the corresponding lung contour, and parameter N may be an integer less than M.

Merely by way of example, the threshold may include one or more of the conditions that a rotation angle is less than or equal to $\pi/180000$, a scaling factor is less than or equal to 0.001, or a translation distance (vector) is less than or equal to 0.01 pixel. The pre-set value may be an integer, such as 90.

Figure 9B:
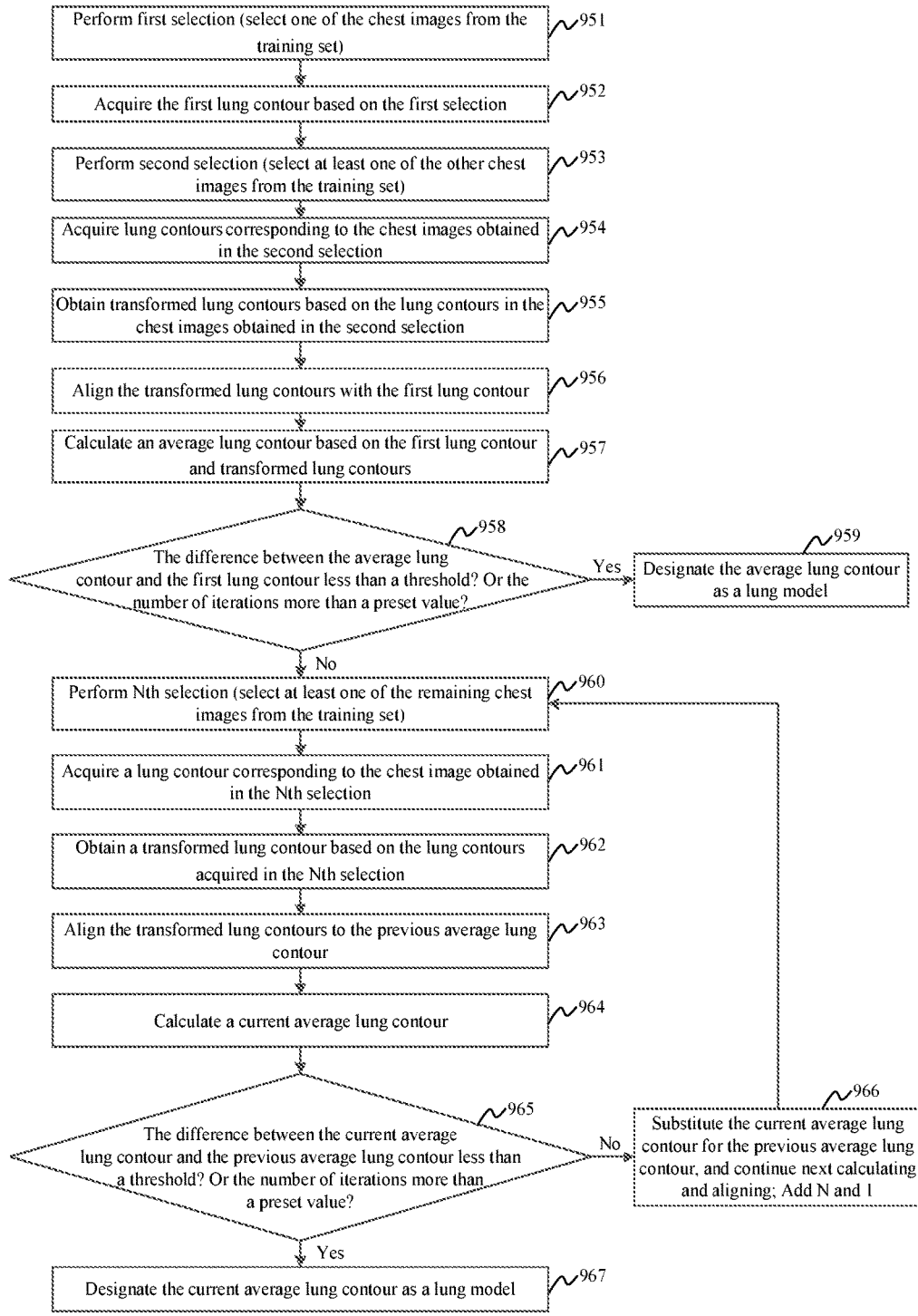
FIG. 9B illustrates a flowchart of an exemplary process for obtaining a lung model according to some embodiments of the present disclosure.

FIG. 9B illustrates a flowchart of an exemplary process for obtaining a lung model according to some embodiments of the present disclosure.

In 951, a first selection may be performed. The first selection may include selecting one of the chest image samples from a training set.

In 952, a first lung contour (reference lung contour) in the chest image sample may be acquired.

In 953, a second selection may be performed. The second selection may include selecting at least one of the other chest image samples from the training set.

In 954, lung contours corresponding to the chest image samples obtained in the second selection may be acquired.

In 955, the lung contours in the chest image samples obtained in the second selection may be processed to obtain transformed (corrected) lung contours. The processing of the lung contours may include performing rotation, scaling and/or translation transformation on the lung contours regarding the first lung contour.

In 956, the transformed (corrected) lung contours may be aligned with the first lung contour.

In 957, an average lung contour may be calculated based on the first lung contour and transformed lung contours. The detailed method of calculating the average lung contour may be found elsewhere in present disclosure.

In 958, the average lung contour and the first lung contour may be compared to get a difference. The difference may be compared with a threshold and number of iterations may be compared with a pre-set value. If the difference is less than the threshold and/or the number of iterations is more than the pre-set value, the average lung contour may be designated as a lung model in 959, otherwise, proceed to 960.

In 960, an Nth selection may be performed. The Nth selection may include selecting at least one of the remaining chest image samples from the training set.

In 961, a lung contour corresponding to the chest image samples obtained in the Nth selection may be acquired.

In 962, the lung contours acquired in the Nth selection may be processed to obtain a transformed (corrected) lung contour. The processing of the lung contour may include performing rotation, scaling and translation transformation on the lung contour regarding the previous average lung contour.

In 963, the transformed (corrected) lung contours may be aligned to the previous average lung contour obtained from the previous selection.

In 964, the current average lung contour may be determined. An exemplary process for determining the current average lung contour may be found elsewhere in present disclosure.

In 965, the current average lung contour and the previous average lung contour may be compared to get a difference. The difference may be compared with a threshold and number of iterations may be compared with a pre-set value. If the difference is less than the threshold or the number of iterations is more than the pre-set value, the current average lung contour may be designated as a lung model in 967, otherwise, proceed to 966.

In 966, one or more of the following operations may be performed:
the current average lung contour may be designated as the previous average lung contour;
the value of N may be increased by 1; and
the process may proceed to 960.

In some embodiments, the threshold may include one or more of the conditions that rotation angle is less than or equal to π/180000, scaling factor is less than or equal to 0.001, or translation distance (vector) is less than or equal to 0.01 pixel. Merely by way of example, the threshold and the pre-set value mentioned in 908, 913, 958, and 965 may be respectively same. N may be an integer greater than two.

Furthermore, if all of the remaining chest image samples in training set have been selected during the Nth selection, the corresponding lung contours acquired in the Nth selection may be performed to obtain transformed (corrected) lung contours, the transformed (corrected) lung contours may be aligned to the previous average lung contour obtained from the first selection to the (N−1)th selection, and the current average lung contour may be designated as the lung model. The processing of the corresponding lung contours may include performing rotation, scaling and translation transformation on the corresponding lung contours regarding the previous average lung contour In some embodiments, the lung model may be obtained and stored in a storing module 1640. The storing module 1640 may output the lung model to an external resource, such as a floppy disk, a hard disk, a CD-ROM, a network server, a cloud server, a wireless terminal, or the like, or any combination thereof.

Referring to FIG. 16, an image segmentation system may include an acquisition module 1610, an outputting module 1620, a processing module 1630, a storing module 1640 and an inputting module 1650.

The storing module 1640 may be configured to store a training set and at least one chest image, wherein the training set include a plurality of chest image samples.

The outputting module 1620 may be configured to display the plurality of chest image samples;

The inputting module 1650 may be configured to annotate feature points at lungs in the chest image samples and acquire contours of the lungs thereof;

The processing module 1630 may be configured to:
obtain a lung model based on the plurality of chest image samples;
pre-process the chest image;
acquire a binary image of boundaries of a lung in the chest image;
perform generalized Hough transform on the binary image to locate initial boundaries of the chest image based on a plurality of lung template and obtain Hough locations;
align the lung model with the Hough location to obtain an alignment result;
apply dynamic programming algorithm to the alignment result to obtain a segmentation result; and
transform the segmentation result back to the original coordinate system.

The processing module 1630 may transfer the information from the storage module to a particular form that may be identified, understood, or executed by the processing module 1630 and it may process the information from the acquisition module 1610 to retrieve data from the storage module. The information from the acquisition module 1610 to the output module may be processed by the storage module firstly so that it may be identified, understood, or executed by the processing module 1630. The above description of the processing module 1630 is merely for exemplary purposes, should not be understood as the only embodiments, and these examples do not limit the scope of the present disclosure.

In some embodiments, the processing module 1630 may be a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an Advanced RISC Machines (ARM), or the like, or any combination thereof.

The storage module may store information related to image processing. In some embodiments, the storage module may perform storage-related functions, such as data consolidation and/or data pre-processing. The storage module may acquire information from or output information to other modules. Merely by way of example, the storage module may receive the data from the acquisition module 1610, and then send it to the processing module 1630, possibly after pre-processing the data. The information stored in storage module may be acquired from or output to an external resource, such as a floppy disk, a hard disk, a CD-ROM, a network server, a cloud server, a wireless terminal, or the like, or any combination thereof.

The inputting module 1650 may be a peripheral device providing data and control signals to the processing module 1630 or the storing module 1640. For example, the input devices may include but not limited to keyboards, mouse, scanners, digital cameras, joysticks, touch screens.

The output module may be a computer hardware device that may output the results of the image processing obtained in the processing module 1630. In some embodiments, the output module may convert the electronically generated information into a human-readable format. The output module may be display devices such as CRT monitors, LCD monitors and displays, gas plasma monitors, televisions, etc.

EXAMPLES

The following examples are provided for illustration purposes, and not intended to limit the scope of the present disclosure.

Example 1

Figure 10:
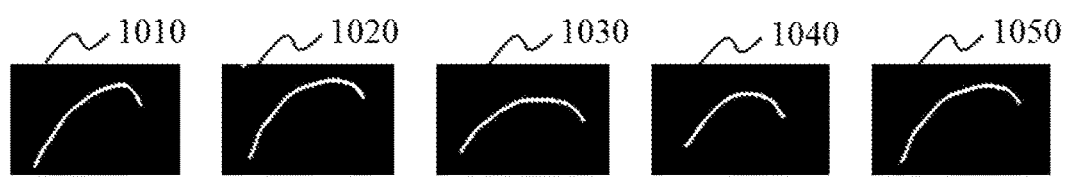
FIG. 10 illustrates some exemplary lung templates according to some embodiments of the present disclosure.

FIG. 10 illustrates some exemplary lung templates according to some embodiments of the present disclosure. As shown in FIG. 10, five upper boundaries of lungs with various shapes and angles were designated as the lung templates 1010, 1020, 1030, 1040, and 1050.

Example 2

Figure 11:
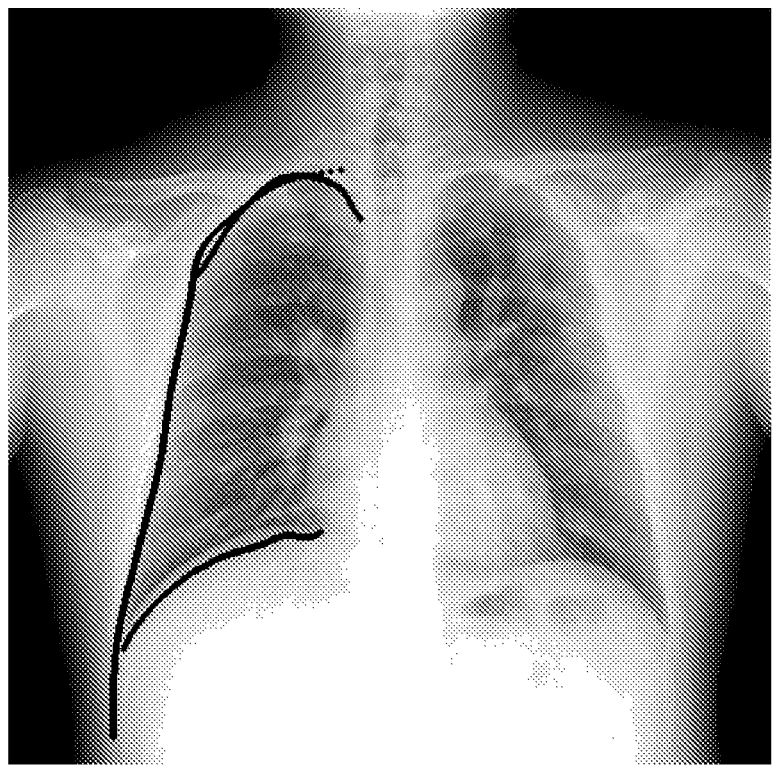
FIG. 11 is an exemplary diagram of Hough location according to some embodiments of the present disclosure.

FIG. 11 is an exemplary diagram of Hough location according to some embodiments of the present disclosure. Generalized Hough transform was employed to locate the boundaries of the lung image, and Hough locations of boundaries (upper boundary, lower boundary, and left boundary) were obtained.

Example 3

Figure 12:
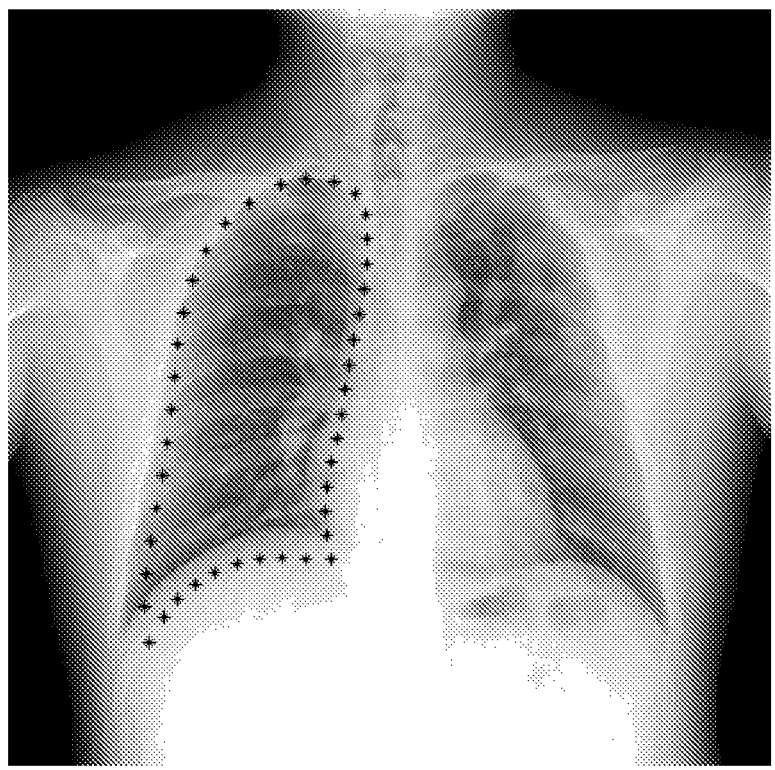
FIG. 12 shows an exemplary alignment result of the lung according to some embodiments of the present disclosure.

FIG. 12 shows an exemplary alignment result of the lung according to some embodiments of the present disclosure. Hough locations in the lung area of chest image was obtained and aligned to obtain an alignment result.

As shown in FIG. 12, the alignment result includes three parts: an outer part, a lower part and an inner part. The outer part was annotated by sixteen feature points (1st-16th point), the lower part was annotated by eight feature points (17th-24th points) and the inner part was annotated by eighteen feature points (25th-42th points). These three parts, as shown in FIG. 12, together formed a contour of the lung. In some embodiments, each of the three parts may be linear interpolated and additional feature points may be obtained. A number of pixel values (or gray scale) along a normal direction of each feature point may be extracted, and a normal matrix may be obtained accordingly. The exemplary diagram of the normal matrix may be found in FIG. 4B and the description thereof. In some embodiments, the number of pixel values extracted may be three, five, eight, ten, twenty and fifty, or other numbers.

Example 4

FIG. 13 is an exemplary diagram of a preliminary lung segmentation according to some embodiments of the present disclosure. FIG. 13 shows a chest image after preliminary lung segmentation in which sections (e.g. upper section 1310, lower section 1320, lateral sections 1330 and 1340) of a lung in the chest image were segmented. FIG. 13 illustrates an exemplary segmentation result of 811 in FIG. 8.

Example 5

Figure 14:
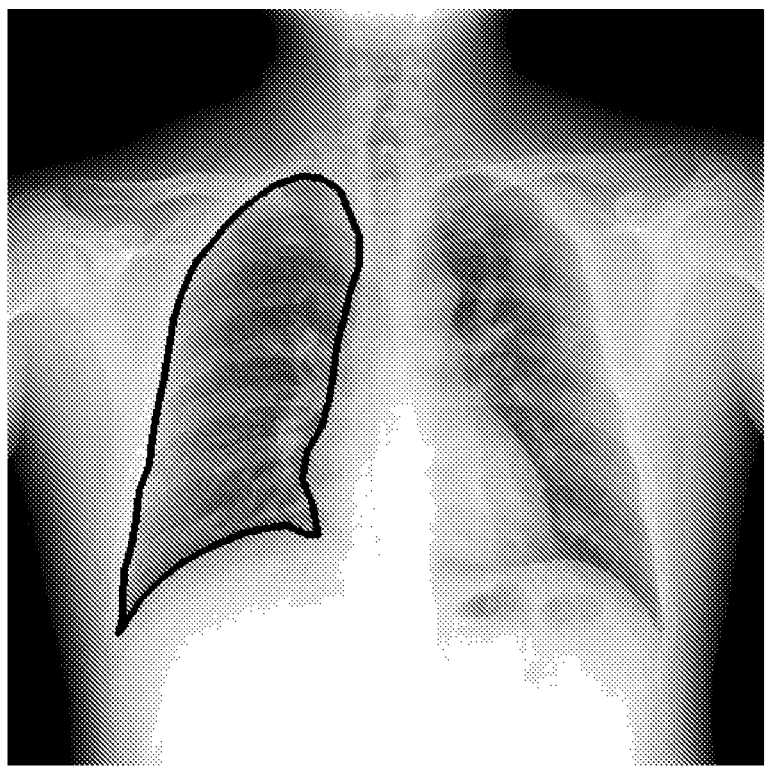
FIG. 14 is an exemplary diagram of a lung segmentation result according to some embodiments of the present disclosure.

FIG. 14 is an exemplary diagram of a lung segmentation result according to some embodiments of the present disclosure. FIG. 14 shows a chest image after a final lung segmentation. The final lung segmentation was obtained by connecting the sections obtained in a preliminary lung segmentation, as illustrated in, for example, FIG. 13 to form a segmented image of a whole lung. FIG. 14 illustrates an example of a final segmentation result of 812 in FIG. 8.

Example 6

Figure 17:
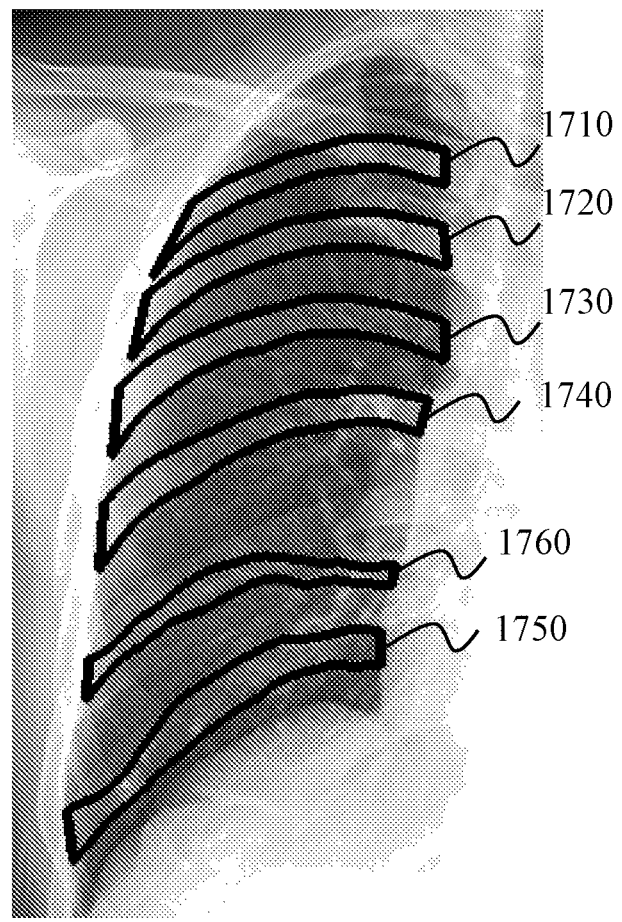
FIG. 17 illustrates exemplary rib segmentation results of different qualities.

FIG. 17 illustrates some exemplary rib segmentation results with different qualities.

Ninety-three chest images (DR images) were processed utilizing the ribs segmentation described herein. A determination was made as to the sensitivity (the number of segmented ribs divided by the total number of ribs inside the lung regions) and the false positives per image for right and left lungs for the dynamic programming algorithm. The dynamic programming algorithm achieved sensitivities of 98.4% and 98.1%, with 0.11 and 0.08 false positives per image, for the right and left lungs, respectively.

For all segmented ribs, a physician subjectively rated the quality of each rib segmentation result with three levels: "1", good; "2", acceptable; and "3", poor based on the similarity between the segmented ribs and the real shape of the corresponding ribs. FIG. 17 illustrates an exemplary lung image on which ribs are segmented. As shown in FIG. 17, rib segmentation result 1710, 1720, 1730, 1740 are evaluated as good, rib segmentation result 1750 is evaluated as acceptable, and rib segmentation result 1760 is evaluated as poor. The quality of rib segmentation is slightly higher in the left lungs than in the right lungs. Overall, more than 90% of the segmented ribs were rated good.

Example 7

FIG. 18A, FIG. 18B, FIG. 18C, and FIG. 18D illustrate some exemplary lung segmentation results with different qualities.

Two hundred seventy chest images (DR images) were processed utilizing the lungs segmentation described herein. The results show that Hough transformation may automatically locate upper boundaries, lower boundaries, and outer boundaries of the lungs. To evaluate the quality of segmentation images, objective ratings by several radiologists and physicists were utilized independently. A four-point rating scale below was then generated based on the objective ratings: "1" Bad, "2" Acceptable, "3" Good, "4" Excellent.

Figure 18A:
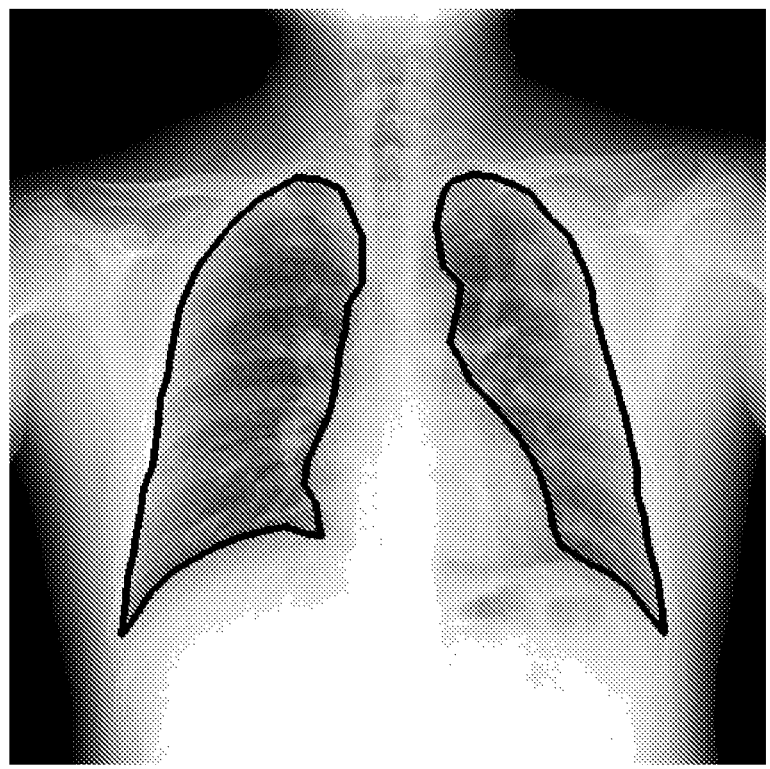
FIG. 18A, FIG. 18B, FIG. 18C, and FIG. 18D illustrate exemplary lung segmentation results of different qualities.
Figure 18B:
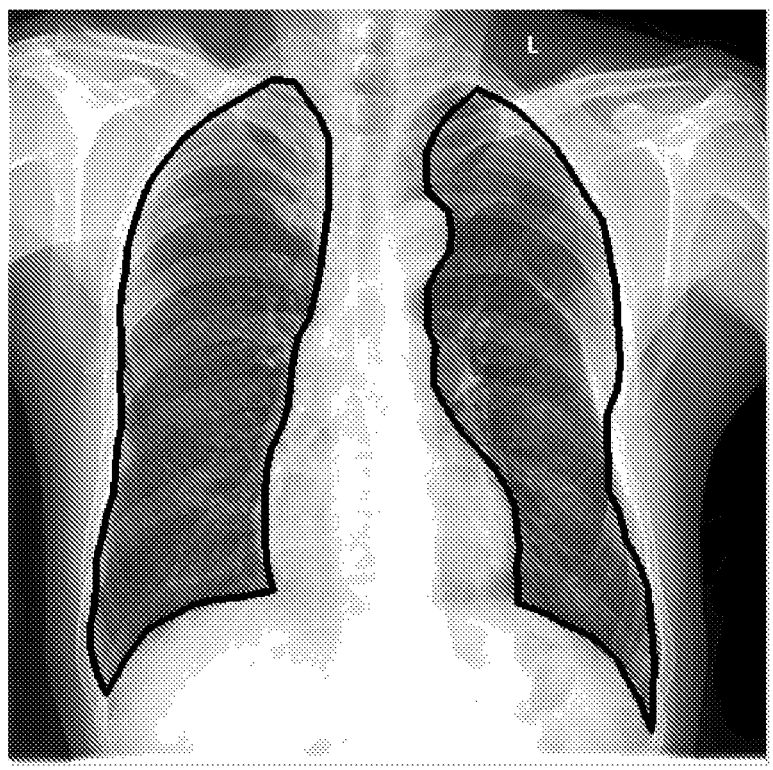
Figure 18C:
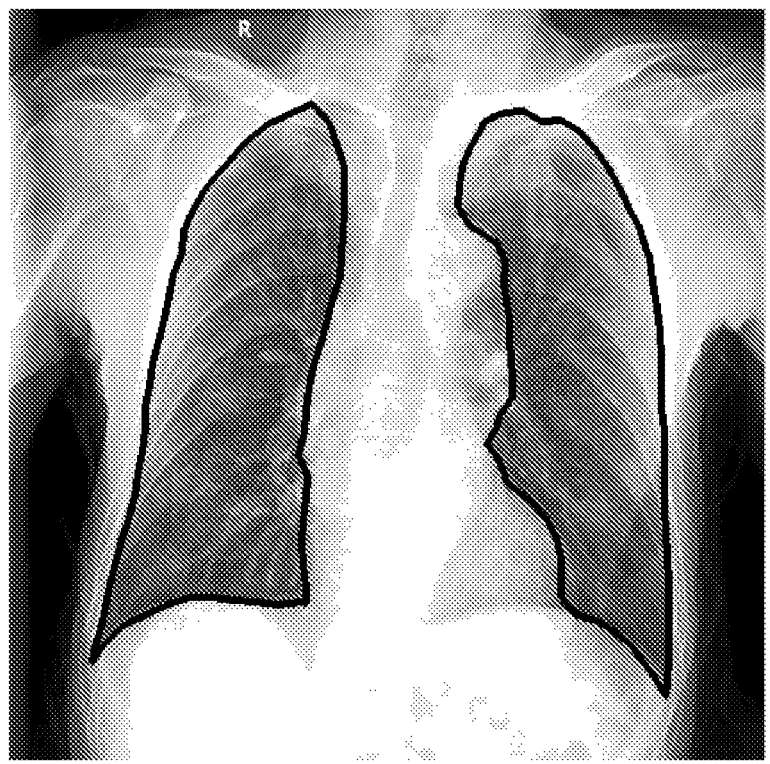
Figure 18D:
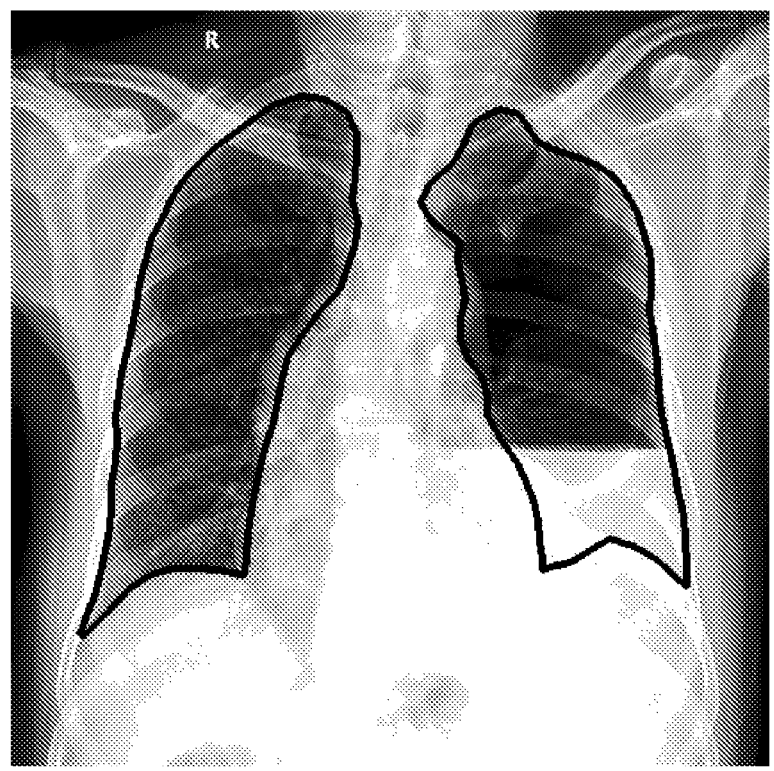

The rating for each case was determined in one of the four categories above based on the average (or the majority) of the ratings provided by multiple observers. The test result on the total 270 data images may be classified into four categories: "excellent," "good," "acceptable" and "bad" as above. FIG. 18A illustrates an exemplary segmented image that evaluated as excellent, in which all the pixels in the boundaries of the lungs were correctly segmented. FIG. 18B illustrates an exemplary segmented image that evaluated as good, in which most of the pixels in the boundaries of the lungs were correctly segmented. FIG. 18C illustrates an exemplary segmented image that evaluated as acceptable, in which some of the pixels in boundaries of the lungs were correctly segmented. FIG. 18D illustrates an exemplary segmented image that evaluated as poor, in which few of the pixels in boundaries of the lungs were correctly segmented. Approximately 95% results are excellent or good.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wire line, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computer including a storage device and a processor for segmenting an image, the method comprising:
    obtaining, by the processor, a lung model;
    obtaining, by the processor, a chest image including a lung;
    pre-processing, by the processor, the chest image;
    acquiring, by the processor, a binary image including a boundary of the lung based on the preprocessed chest image;
    performing, by the processor, generalized Hough transform on the binary image to locate an initial boundary of the lung in the chest image to obtain a Hough location of the lung;
    aligning, by the processor, the lung model to the Hough location of the lung to obtain an alignment result;
    applying, by the processor, a dynamic programming algorithm to the alignment result to obtain a segmentation result; and
    transforming, by the processor, the segmentation result back to a coordinate system of the chest image,
    wherein the lung model is obtained by the processor by:
        obtaining a training set, wherein the training set includes a plurality of chest image samples;
        selecting a first chest image sample from the training set;
        acquiring a first lung contour in the first chest image sample;
        selecting a plurality of the second chest image samples from the training set;
        acquiring a plurality of second lung contours, a second lung contour corresponding to a second chest image;
        processing the plurality of second lung contours to obtain transformed second lung contours;
        aligning the transformed second lung contours with the first lung contour;
        determining an average lung contour;
        determining a difference between the average lung contour and the first lung contour;
        comparing the difference with a threshold;
        determining that the difference is smaller than the threshold to obtain a first determination result; and
        designating, based on the first determination result, the average lung contour as the lung model.
2. The method of claim 1, further comprising:
    determining that the difference is larger than or equal to the threshold to obtain a second determination result;
    performing, based on the second determination result, operations including
        designating the average lung contour as a previous average lung contour;
        performing rotation, scaling and translation transformation on the first lung contour and the plurality of second lung contours with respect to the previous average lung contour to obtain current transformed lung contours;
        aligning the current transformed lung contours with the previous average lung contour;
        determining a current average lung contour; and
        determining a difference between the rotation, scaling and translation transformation for the current average lung contour and the previous average lung contour;
        comparing the difference with the threshold;
        determining that the difference is smaller than the threshold to obtain a third determination result; and
        designating, based on the third determination result, the current average lung contour as the lung model.
3. The method of claim 1, wherein two lungs in two chest image samples of the plurality of chest image samples are each annotated by a same number of feature points.
4. The method of claim 3, wherein the feature points on the two lungs of the chest image sample are annotated at similar locations.
5. The method of claim 3, wherein the feature points are annotated at the corners, the highest point and the lowest point on a contour of each lung in the chest image samples.
6. The method of claim 1, wherein the pre-processing the chest image comprises:
    filtering the chest image by a Gaussian filter to obtain a filtered image;
    subtracting the filtered image from the chest image to obtain a subtracted image;
    adding an average gray scale of the filtered image to the subtracted image to obtain a background removed image; and
    performing a bilateral filtering operation to the background removed image to obtain a pre-processed chest image.
7. The method of claim 6, further comprising:
    obtaining a template corresponding to the boundary of the lung in the binary image;
    identifying a gravity point of the template;
    identifying a first point other than the gravity point on the template;
    performing generalized Hough transform to locate a second point in the binary image that corresponds to the first point;
    determining, based on the second point, a third point in a Hough space; and
    increasing a gravity value of the third point by one.
8. The method of claim 1, the acquiring a binary image comprising:
    applying a boundary edge enhancement operator to the chest image to obtain a gradient image; and
    generating the binary image based on the gradient image.
9. The method of claim 8, the generating the binary image based on the gradient image comprising
    designating pixels in the gradient image whose values are at least 15% of the highest values in the gradient image as belonging to the boundary of the lung.
10. A method implemented on a computer including a storage device and a processor for segmenting an image, the method comprising:

obtaining, by the processor, a chest image including a plurality of ribs;

pre-processing, by the processor, the chest image;

acquiring, by the processor, a binary image based on the pre-processed chest image;

obtaining, by the processor, a plurality of rib templates;

performing, by the processor, generalized Hough transform to obtain a gravity value based on each of the plurality of rib templates;

selecting, by the processor, one of the plurality of rib templates as a representative rib template based on the gravity values;

selecting, by the processor, a representative rib with respect to one rib in the binary image based on the representative rib template;

generating, by the processor, a standard rib template based on the representative rib;

performing, by the processor, generalized Hough transform based on the standard rib template to locate a lower boundary of a rib in the chest image to obtain a Hough location of the rib;

aligning, by the processor, the standard rib template to the Hough location to obtain an alignment result;

applying, by the processor, a bilateral dynamic programming algorithm to the alignment result to obtain a segmentation result; and transforming, by the processor, the segmentation result to a coordinate system of the chest image.

11. The method of claim 10, further comprising applying a Sobel edge enhancement filter to enhance the lower boundaries of the ribs.

12. The method of claim 11, wherein the value of pixels in a top section and a bottom section of the lung in the chest image is set to zero.

13. The method of claim 12, further comprising performing a bilateral dynamic programming algorithm to delineate the lower boundary and the upper boundary of a rib simultaneously, with a constrained dimension between the upper boundary and the lower boundary of the rib maintained to be a pre-set value.

14. The method of claim 13, wherein the constrained dimension has a value from eleven to twenty pixels.

15. The method of claim 10, wherein the distance between two adjacent ribs is assumed to be ten percent of the height of the lung.

16. A system comprising:

a storing device configured to store a training set and at least one chest image, wherein the training set has a plurality of chest image samples;

a display device configured to display the plurality of the chest image samples;

an input device configured to annotate feature points at lungs in the chest image samples and acquire contours of the lungs thereof;

a processor configured to perform a lung segmentation, the lung segmentation including:
  pre-processing the chest image;
  acquiring a binary image of boundaries of a lung in the chest image;
  performing generalized Hough transform on the binary image to locate initial boundary of the lung to obtain a Hough location;
  aligning the lung model to the Hough location to obtain an alignment result;
  applying dynamic programming algorithm to the alignment result to obtain a segmentation result; and
  transforming the segmentation result back to a coordinate system of the chest image, wherein the lung model is obtained by the processor by:
  obtaining the training set;
  selecting a first chest image sample from the training set;
  acquiring a first lung contour in the first chest image sample;
  selecting a plurality of the second chest image samples from the training set;
  acquiring a plurality of second lung contours, a second lung contour corresponding to a second chest image;
  processing the plurality of second lung contours to obtain transformed second lung contours;
  aligning the transformed second lung contours with the first lung contour;
  determining an average lung contour;
  determining a difference between the plurality of second lung contours and the first lung contour;
  comparing the difference with a threshold; determining that the difference is smaller than the threshold to obtain a first determination result; and
  designating, based on the first determination result, the average lung contour as the lung model.

17. The system of claim 16, wherein the processor is further configured to segment ribs based on the lung segmentation.

18. The system of claim 17, wherein the processor is further configured to subtract the ribs from the lung.

19. The system of claim 17, wherein the display device displays the lung together with ribs, or displays the lung without the ribs.

* * * * *